US009518095B2

(12) United States Patent
Emmerling et al.

(10) Patent No.: US 9,518,095 B2
(45) Date of Patent: Dec. 13, 2016

(54) SCALABLE FERMENTATION PROCESS

(71) Applicant: KUROS BIOSCIENCES AG, Schlieren (CH)

(72) Inventors: Marcel Emmerling, Schlieren (CH); Frank Hennecke, Dietlikon (CH); Holger Pfründer, Zürich (CH); Martin Rhiel, Bonstetten (CH); Philipp Steiner, Schlieren (CH)

(73) Assignee: KUROS BIOSCIENCES AG (CH)

( * ) Notice: Subject to any disclaimer, the term of this patent is extended or adjusted under 35 U.S.C. 154(b) by 0 days.

(21) Appl. No.: 14/247,097

(22) Filed: Apr. 7, 2014

(65) Prior Publication Data
US 2015/0104827 A1    Apr. 16, 2015

Related U.S. Application Data

(63) Continuation of application No. 13/335,008, filed on Dec. 22, 2011, now abandoned, which is a continuation of application No. 11/921,023, filed as application No. PCT/EP2006/062628 on May 24, 2006, now abandoned.

(30) Foreign Application Priority Data

May 26, 2005 (EP) .................................. 05011416
Jul. 21, 2005 (EP) .................................. 05106729

(51) Int. Cl.
| C12N 7/01 | (2006.01) |
| C12N 15/11 | (2006.01) |
| A61K 35/76 | (2015.01) |
| C07K 14/005 | (2006.01) |
| C12N 7/00 | (2006.01) |
| A61K 38/00 | (2006.01) |
| A61K 39/00 | (2006.01) |

(52) U.S. Cl.
CPC ............. C07K 14/005 (2013.01); C12N 7/00 (2013.01); *A61K 2039/5256* (2013.01); *A61K 2039/5258* (2013.01); *C12N 2795/00023* (2013.01); *C12N 2795/00051* (2013.01); *C12N 2795/10051* (2013.01); *C12N 2795/10061* (2013.01); *C12N 2795/18022* (2013.01); *C12N 2795/18052* (2013.01)

(58) Field of Classification Search
None
See application file for complete search history.

(56) References Cited

U.S. PATENT DOCUMENTS

| 5,304,723 A | 4/1994 | Schmid et al. |
| 5,356,792 A | 10/1994 | Maeda et al. |
| 6,159,728 A | 12/2000 | Stockley et al. |
| 6,291,245 B1 | 9/2001 | Kopetzki et al. |
| 6,833,260 B1 | 12/2004 | Ruch et al. |
| 7,419,659 B2 | 9/2008 | Popplewell |
| 7,572,451 B2 * | 8/2009 | Bachmann ......... A61K 47/4833 424/185.1 |
| 2004/0058348 A1 * | 3/2004 | Bogin .................... C12N 15/67 435/6.16 |
| 2004/0091976 A1 | 5/2004 | Deng et al. |
| 2006/0024796 A1 | 2/2006 | Hoshino et al. |
| 2006/0251677 A1 * | 11/2006 | Bachmann ......... A61K 39/0011 424/204.1 |
| 2006/0280724 A1 | 12/2006 | Ferguson et al. |
| 2007/0184068 A1 | 8/2007 | Renner et al. |
| 2010/0047870 A1 | 2/2010 | Niphadkar et al. |

FOREIGN PATENT DOCUMENTS

| WO | WO 92/07077 | 4/1992 |
| WO | WO 92/13081 | 8/1992 |
| WO | WO02/056905 A2 | 7/2002 |
| WO | WO2004/007538 A2 | 1/2004 |

OTHER PUBLICATIONS

Amann, E., Brosius, J., Ptashne, M., "Vectors bearing a hybrid trp-lac promoter useful for regulated expression of cloned genes in *Escherichia coli.*" *Gene*, vol. 25(2-3) pp. 167-178, 1983, Elsevier Science Publishers, Netherlands.
Broslus, J, Erfle, M, Storella, J., "Spacing of the -10 and -35 regions in the *tac* promoter. Effect on its in vivo activity." *J Biol Chem*, vol. 260(6) pp. 3539-3541, 1985, The American Society of Biological Chemists, U.S.A.
Cielens, I, Ose, V, Petrovskis, I, Strelnlkova, A, Renhofa, R, Kozlovska, T, Pumpens, P. "Mutilation of RNA phage Qbets virus-like particles: from icosahedrons to rods." *FEBS Lett*, vol. 482(3) pp. 261-264, 2000, Elsevier Science B.V., Netherlands.
Dalbøge, H, Carlsen, S, Jensen, EB, Christensen, T, Dahl, HH., "Expression of recombinant growth hormone in *Escherichia coli*: effect of the region between the Shine-Dalgarno sequence and the ATG initiation codon." *DNA*, vol. 7(6) pp. 399-405, 1988, Mary Ann Liebert, Inc., U.S.A.
De Boer, HA, Cornstock, LJ, Vasser, M., "The *tac* promoter: a functional hybrid derived from the *trp* and *lac* promoters." *Proc Natl Acas Sci U S A*, vol. 80(1) pp. 21-25, 1983, National Academy of Sciences, USA.
Donovan, RS, Robinson, CW, Glick, BR., "Optimizing the expression of a monoclonal antibody fragment under the transcriptional control of the *Escherichia coli lac* promoter." *Can J Microbiol*, vol. 46(6) pp. 532-541, 2000, National Research Council, Canada.
(Continued)

*Primary Examiner* — Anand Desai
*Assistant Examiner* — Samuel Liu
(74) *Attorney, Agent, or Firm* — Medler, Ferro, Woodhouse & Mills PLLC

(57) ABSTRACT

This invention provides a robust fermentation process for the expression of a capsid protein of a bacteriophage which is forming a VLP by self-assembly, wherein the process is scalable to a commercial production scale and wherein the expression rate of the capsid protein is controlled to obtain improved yield of soluble capsid protein. This is achieved by combining the advantages of fed-batch culture and of lactose induced expression systems with specific process param- (Continued)

eters providing improved repression of the promoter during the growth phase and high plasmid retention throughout the process.

20 Claims, 1 Drawing Sheet

(56) References Cited

OTHER PUBLICATIONS

Donovan, RS, Robinson, CW, Glick, BR., "Review: optimizing Inducer and culture conditions for expression of foreign proteins uner the control of the *lac* promoter." *J Ind Microbiol*, vol. 16(3) pp. 145-154, 1996, Society for Industrial Microbiology, USA.
Glascock, CB, Weickert, MJ., "Using chromosomal *laclQ1* to control expression of genes on high-copy-number plasmids in *Escherichia coli*." *Gene* vol. 223(1-2) pp. 221-231, 1998, Elsevier Science B.V., Netherlands.
Goldstein, MA, Dol, RH., "Prokaryotic promoters in biotechnology." *Biotechnol Annu Rev*. vol. 1 pp. 105-128, 1995, Elsevier Science B.V., Netherlands.
Golmohammadi, R, Fridborg, K, Bundule, M, Valegård, K, Liljas, L., "The crystal structure of bacteriophage Q beta at 3.5 A resolution." *Structure*, vol. 4(5) pp. 543-554, 1996, Current Biology Ltd., United Kingdom.
Heal, K, Hill, H, Stockley, PG, Hollingdale, MR, Taylor-Robinson, AW., "Expression and immunogenicity of a liver stage malaria epitope presented as a foreign peptide on the surface of RNA-free MS2 bacteriophage capsids." *Vaccine*, vol. 18 pp. 251-258, 2000, Elsevier Science Ltd., Netherlands.
Kastelein, RA, Berkhout, B, Overbeek, GP, van Duin, J., "Effect of the sequence upstream from the ribosome-binding site on the yield of protein from the cloned gene for phage MS2 coat protein." *Gene*, vol. 23(3) pp. 245-254, 1983, Elsevier Science Publishers B.V., Netherlands.
Kopetzki, E, Schumacher, G, Buckel, P., "Control of formation of active soluble or inactive Insoluble baker's yeast alpha-glucosidase PI in *Escherichia coli* by induction and growth conditions." *Mol Gen Genet*, vol. 216(1) pp. 149-155, 1989, Springer-Verlag, Germany.
Kozlovska, TM, Clelens, I, Dreiling, D, Dislers, A, Baumanis, V, Osa, V, Pumpens, P., "Recombinant RNA phage Q beta capsid particles synthesized and self-assembled in *Escherichia coli.*" *Gene*, vol. 173(1) pp. 133-137, 1993, Elsevier Science B.V., Netherlands.
Kozlovska, TM, Cielens, I, Vasiljeve, I, Streinikova, A, Kazaks, A, Dislers, A, Drellina, D, Ose, V, Gusars, I, Pumpens, P., "RNA phage Q beta coat protein as a carrier for foreign epitopes." *Intervirology*, vol. 39(1-2) pp. 9-15, 1996, Karger AG, Basel, Switzerland.
Kozlovskaya, TM, et al., "Formation of capsid-like structures as a result of the expression of a cloned envelope protein gene from RNA-containing bacteriophage fr." Dokl. Akad. Nauk. SSSR, vol. 287 pp. 452-455, 1986.
Makrides, SC., "Strategies for achieving high-level expression of genes in *Escherichia coli.*" *Microbiol Rev*, vol. 60(3) pp. 512-538, 1996, American Society for Microbiology, USA.
Maslico, RA, Talbot, SJ, Stockley, PG., "Multiple presantation of foreign peptides on the surface of an RNA-free spherical bacteriophage capsid." *J Gen Virol*, vol. 74 pp. 541-548, 1993, Society for General Microbiology, Great Britain.
Menzella, HG, Ceccarelli, EA, Gramajo, HC., "Novel *Escherichia coli* strain allows efficient recombinant protein production using lactoss as inducer." *Biotechnol Bioeng*, vol. 82(7) pp. 809-817, 2003, Wiley Perlodicals, Inc., USA.
Molinari, P, Marusic, C, Lucioli, A, Tavazza, R, Tavazza, M., "Identification of artichoke mottled crinkle virus (AMCV) proteins required for virus replication: complementation of AMCV p33 and p92 replication-defective mutants." *J Gen Virol*, vol. 79 pp. 639-647, 1998, Society for General Microbiology, Great Britain.

Peabody, DS, Al-Bitar, L., "Isolation of viral coat protein mutants with altered assembly and aggregation properties." *Nucleic Acids Res*, vol. 29(22) pp. E113:1-7, 2001, Oxford University Press, Great Britain.
Pumphrey, B, and Jullen, C., "An Introduction to Fermentation—Fermentation Basics New Brunswick Scientific (web resources)." vol. 0(NA) pp. NA, 1996 (cite in International Search Report for PCT/EP2006/062628).
Pushko, P, Kozlovskaya, T, Sominskaya, I, Brede, A, Stankevica, E, Ose, V, Pumpens, P, Grens, E., "Analysis of RNA phage *fr* coat protein assembly by Insertion, deletion and substitution mutagenesis." *Protein Eng*, vol. 6(8) pp. 883-891, 1993, Oxford University press, Great Britain.
Ringquist, S, Shinedling, S, Barrick, D, Green, L, Binkley, J, Stormo, GD, Gold, L., "Translation initiation in *Escherichia coli*: sequences within the ribosome-binding site." *Mol Microbiol*, vol. 6(9) pp. 1219-1229, 1992. Wiley-Blackwell, USA.
Schwarz, K, Meijerink, E, Speiser, DE, Tissot, AC, Clelens, I, Renhof, R, Dishlere, A, Pumpens, P, Bachmann, MF., "Efficient homologus prime-boost stratgies for T cell vaccination based on virus-like particles." *Eur J Immunol*, vol. 35(3) pp. 816-821, Mar. 2005, Wiley-VCH Verlag GmbH & Co., KGaA, Weinheim, Germany.
Stevens, RC., "Design of high-throughput methods of protein production for structural biology." *Structure*, vol. 8(9) pp. R177-R185, 2000, Elsevier Science Ltd., Netherlands.
Stoll, E, Wilson, KJ, Reiser, J, Weissmann, C., "Revised amino acid sequence of Qbeta coat protein between positions 1 and 60." *J Biol Chem*, vol. 252(3) pp. 990-993, 1977, The American Society of Biological Chemists, U.S.A.
Vasiljeva, I, Kozlovska, T, Clelens, I, Streinlkova, A, Kazaks, A, Ose, V, Pumpens, P., "Mosaic Qbeta coats as a new presentation model." *FEBS Lett*, vol. 431(1) pp. 7-11, 1998, Elsevier Science B.V., Netherlands.
Wang, ZW, Law, WS, Chao, YP., "Improvement of the thermoregulated T7 expression system by using the heat-sensitive *lacI*" *Biotechnol Prog*, vol. 20(5) pp. 1352-1358, 2004, American Chemical Society and American Institute of Chemical Engineers, USA.
International Search Report for PCT/EP2006/062628, European Patent Office, the Netherlands, mailed Dec. 19, 2006.
Kozlovskaya, T.M., et al., "Formation of capsid-like structures as a result of the expression of a cloned envelope protein from RNA-containing bacteriophage fr," STNEasy, Accession No. 1986:19892, CAplus English abstract (1986).
Attachment 1 (2010) alignment with instant SEQ ID No. 5, p. 1.
Attachment 2 (2010) alignment with instant SEQ ID No. 2, pp. 1-2.
Attachment 1 (2013) amino acid sequence alignment for SEQ ID No. 2, p. 1.
Attachment 2 (2013) amino acid sequence alignment for SEQ ID Nol. 2, p. 1.
Donahue et al., "BL21-SI Competent Cells for Protein expression in *E. coli,*" *Focus* 21(2):49-51 (1999).
Hannig et al., "Strategies for optimizing heterologous protein expression in *Escherichia coli,*" *Trends Biotech* 16:54-60 (1998).
Hong et al., "Effects of in-vitro protein stabilizers on the overexpression of recombinant beta-lactamase in *Escherichia coli,*" *Biotechnol. Lett* 14(5):345-350 (1992).
Lim et al., "The RNA-binding Site of Bacteriophage Q$\beta^2$ Coat Protein," *J. Biol. Chem*, 271:31839-31845 (1996).
Lima et al., "Dissecting the role of protein-protein and protein-nucleic acid interactions in MS2 bacteriophage stability," *FEBS J. m* 273:1463-1475 (2006).
Lindemann et al., "Evolution of bacteriophage in continuous culture: a model system to test antiviral gene therapies for the emergence of phage escape mutants," *J. Virol*. 76(11):5784-5792 (2002).
Long et al., "Cellular microcystin content in N-limited Microcystis aeruginosa can be predicted from growth rage," *Appl. Environ. Microbiol*. 67(1):278-283 (2001).
Peabody et al., "Immunogenic display of diverse peptides on virus-like particles of RNA phage MS2," *J. Mol. Biol*. 380(1):253-263 (2008).

(56) References Cited

OTHER PUBLICATIONS

Sidhu et al., "Exploring and designing protein function with restricted diversity," *Curr. Opin. Chem. Biol.* 11:347-354 (2007).
Schwienhorst et al, "Growth kinetics of a bacteriophage in continuous culture," *Biotechnol. Bioeng* 50(2):217-221 (1996).
Wikipedia Bacteriophage, en.wikipedia.org/wild/Bacteriophage:1-9 (2011).

* cited by examiner

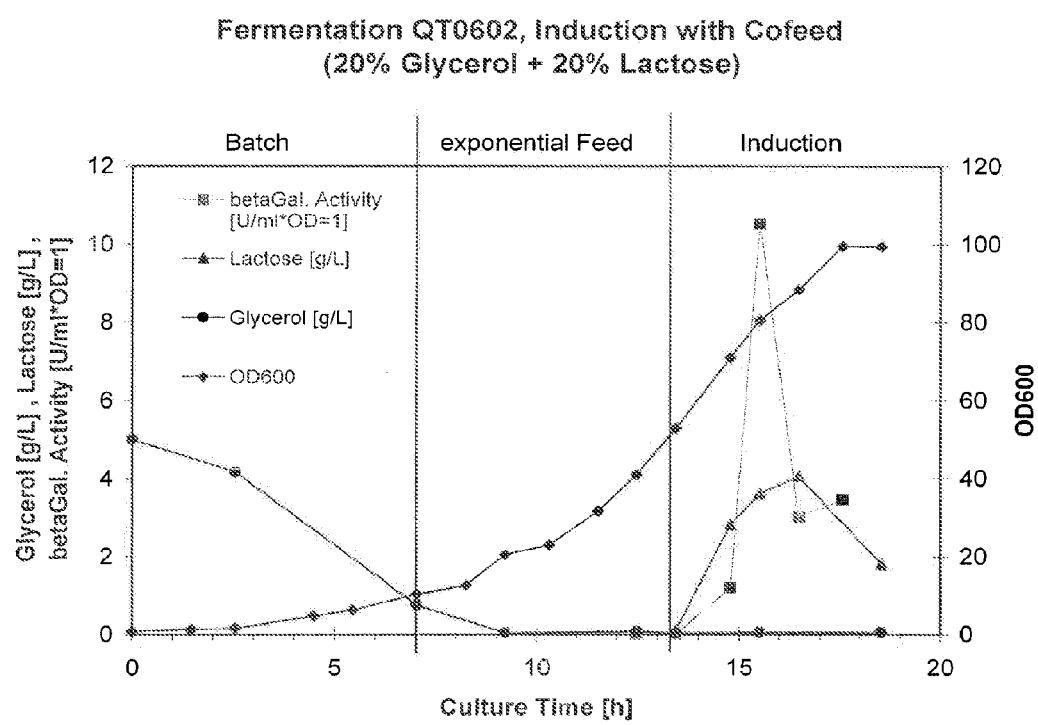

SCALABLE FERMENTATION PROCESS

FIELD OF THE INVENTION

This invention is related to the field of protein expression and fermentation technology. A process for the efficient expression of recombinant bacteriophage capsid protein in a bacterial host is described. The process leads to high yield of recombinant capsid protein which is capable of forming a virus-like particle (VLP) by self-assembly. Furthermore, the process is scalable from laboratory scale to fermenter volumes larger than 50 liters.

BACKGROUND OF THE INVENTION

Recent vaccination strategies make use of viruses or virus-like-particles (VLPs) to enhance the immune response towards antigens. For example, WO02/056905 demonstrates the utility of VLPs as a carrier to present antigens linked thereto in a highly ordered repetitive array. Such antigen arrays can cause a strong immune response, in particular antibody responses, against the linked antigen and are even capable of breaking the immune system's inherent tolerance towards self antigens. Such antigen arrays are therefore useful in the production of vaccines for the treatment of infectious diseases and allergies as well as for the efficient induction of self-specific immune responses, e.g. for the treatment of cancer, rheumatoid arthritis and various other diseases.

As indicated in WO02/056905 capsid proteins of bacteriophages are particularly suited as antigen carrier. They have been shown to efficiently self-assemble into VLPs upon expression in a bacterial host (Kastelein et al. 1983, Gene 23:245-254; Kozlovskaya et al. 1986, Dokl. Akad. Nasik SSSR 287:452-455). Moreover, capsid proteins of bacteriophages such as derived from fr (Pushko et al. 1993, Protein Engineering 6(8)883-891), Qβ (Kozlovska et al. 1993, Gene 137:133-137; Ciliens et al. 2000, FEBS Letters 24171:1-4; Vasiljeva et al 1998, FEBS Letters 431:7-11) and MS-2 (WO92/13081; Mastico et al. 1993, Journal of General Virology 74:541-548; Heal et al. 2000, Vaccine 18:251-258) have been produced in bacterial hosts using inducible promoters such as the trp promoter or a trp-T7 fusion (in the case of fr and Qb) or the the promoter using IPTG as inducer substance (in the case of MS-2). The use of inducible promoters is beneficial, to avoid possible toxic effects of the recombinant capsid protein and the metabolic burden of protein expression which both might reduce the growth of the bacterial expression host and, ultimately, the yield of expressed protein.

However, the expression systems used so far for the expression of capsid proteins of bacteriophages have been applied in small scale fermentations, i.e. in laboratory scale and small batch cultures with volumes of typically clearly below 1 liter. An scale up of these systems comprising volumes of 50 liter and more is expected to diminish in a great extent the respective capsid protein yield due to increased promoter leakage and/or lowered plasmid retention.

A further problem associated with commercially desired high-level expression and rapid accumulation of recombinant capsid proteins of bacteriophages is the formation of incorrectly folded protein species and the formation of so called inclusion bodies, i.e. protein aggregates, which are insoluble and which may hamper further downstream processes. Thus, for bacteriophage MS-2 coat protein the formation of protein aggregates and of protein species which lost their ability to self-assemble to VLPs have been reported when the protein was expressed under the control of the strong T7 promoter after IPTG induction using the pET expression system (Peabody & Al-Bitar 2001, Nucleic Acid Research 29(22):e113).

High expression rates of the recombinant capsid protein may therefore have a negative impact on the yield of correctly assembled VLPs. The production of VLP-based vaccines in a commercial scale requires, therefore, the establishment of an efficient, and in particular scalable fermentation process for the expression of recombinant capsid protein of bacteriophages leading to a product of constant quality and purity having the capability of self-assembling into VLPs, whereby the formation of insoluble fractions of the capsid protein is minimised or avoided.

Therefore, it is an object of the present invention to provide a process for expression of a recombinant capsid protein of a bacteriophage which avoids or minimizes the disadvantage or disadvantages of the prior art processes, and in particular, which is scalable to a commercial scale and still leading to a product of constant quality and purity and the capability of self-assemblance to VLPs, and wherein the formation of insoluble fraction of the capsid protein is minimised or avoided.

SUMMARY OF THE INVENTION

The invention relates to a process for expression of a recombinant capsid protein of a bacteriophage, or a mutant or fragment thereof being capable of forming a VLP by self-assembly, said process comprising the steps of: a.) introducing an expression plasmid into a bacterial host, wherein said expression plasmid comprises an expression construct, wherein said expression construct comprises (i) a first nucleotide sequence encoding said recombinant capsid protein, or mutant or fragment thereof, and (ii) a promoter being inducible by lactose; b.) cultivating said bacterial host in a medium comprising a major carbon source; wherein said cultivating is performed in batch culture and under conditions under which said promoter is repressed by lacI, wherein said lacI is overexpressed by said bacterial host; c.) feeding said batch culture with said major carbon source; and d.) inducing said promoter with an inducer, wherein preferably said feeding of said batch culture with said major carbon source is continued.

This invention provides a robust fermentation process for the expression of a capsid protein of a bacteriophage which is forming a VLP by self-assembly, wherein the process is scalable to a commercial production scale and wherein the expression rate of the capsid protein leads to improved yield of soluble capsid protein. This is, in particular, achieved by improved repression of the promoter during the growth phase and high plasmid retention throughout the process. The expression system further avoids formation of insoluble protein aggregates by limiting the maximum expression rate occurring during the production phase.

In a preferred embodiment said bacteriophage is a RNA bacteriophage. More preferably, said RNA bacteriophage is selected from the group consisting of: a.) bacteriophage Qβ; b.) bacteriophage AP205; c.) bacteriophage fr; d.) bacteriophage GA; e.) bacteriophage SP; f.) bacteriophage MS2; g.) bacteriophage M11; h.) bacteriophage MX1; i.) bacteriophage NL95; j.) bacteriophage f2; k.) bacteriophage PP7 and l.) bacteriophage R17. Preferably, said RNA bacteriophage is Qβ. More preferably said recombinant capsid protein comprises or alternatively consists of an amino acid sequence selected from the group consisting of SEQ ID NO:5, SEQ ID NO:7, SEQ ID NO:8, SEQ ID NO:9, SEQ ID NO:10, and SEQ ID NO:11. Still more preferably said recombinant capsid protein comprises SEQ ID NO:5, most preferably said recombinant capsid protein consists of SEQ ID NO:5.

In a further preferred embodiment said recombinant capsid protein comprises or alternatively consists of an amino acid sequence selected from the group consisting of SEQ ID NO:12, SEQ ID NO:13, and SEQ ID NO:14. More preferably said recombinant capsid protein comprises SEQ ID NO:12, most preferably said recombinant capsid protein consists of SEQ ID NO:12.

In another embodiment of the present invention, said expression construct comprises a first stop codon, and wherein said first stop codon is TAA, and wherein preferably said TAA is located directly 3' of said first nucleotide sequence.

In a further embodiment said expression construct comprises a first stop codon and a second stop codon, wherein said first stop codon is located directly 3' of said first nucleotide sequence and wherein said second stop codon is located directly 3' of said first stop codon, and wherein at least one of said first or second stop codon is TAA.

In a further embodiment said expression construct comprises a first nucleotide sequence and a second nucleotide sequence, wherein said first nucleotide sequence is encoding a recombinant capsid protein, preferably Qβ CP, or a mutant or fragment thereof, and wherein said second nucleotide sequence is encoding any other protein, preferably the Qβ A1 protein or a mutant or fragment thereof, and wherein said first and said second nucleotide sequence are separated by exactly one sequence stretch comprising at least one TAA stop codon. In a preferred embodiment said expression construct comprises or alternatively consists of the nucleotide sequence of SEQ ID NO:6.

In a further embodiment said expression plasmid comprises or, more preferably, consists of the nucleotide sequence of SEQ ID NO:1.

In one embodiment of the invention said promoter is selected from the group consisting of the a.) tac promoter; b.) trc promoter; c.) tic promoter; d) lac promoter; e.) lacUV5 promoter; f.) $P_{syn}$ promoter; g.) $lpp^a$ promoter; h.) lpp-lac promoter; i.) T7-lac promoter; j.) T3-lac promoter; k.) T5-lac promoter; and l.) a promoter having at least 50% sequence homology to SEQ ID NO:2. In a preferred embodiment said promoter has at least 50%, 60%, 70%, 80, 90, or 95%, preferably 98 to 100%, most preferably 99% sequence homology to SEQ ID NO:2. In a further preferred embodiment said promoter is selected from the group consisting of tic promoter, trc promoter and tac promoter. Even more preferably said promoter is the tac promoter. Most preferably said promoter comprises or alternatively consists of the nucleotide sequence of SEQ ID NO:2.

In one embodiment said major carbon source is glucose or glycerol, preferably glycerol.

In one embodiment said feeding of said batch culture is performed with a flow rate, wherein said flow rate increases with an exponential coefficient μ, and wherein preferably said exponential coefficient μ is below $μ_{max}$.

In a further embodiment said inducing of said promoter is performed by co-feeding said batch culture with said inducer, preferably lactose and said major carbon source, preferably glycerol, at a constant flow rate.

In a further embodiment said inducing of said promoter is performed by co-feeding said batch culture with said inducer, preferably lactose and said major carbon source, preferably glycerol, at an increasing flow rate.

In a further embodiment said inducer is lactose, wherein preferably said lactose and said major carbon source are co-fed to said batch culture in a ratio of about 2:1 to 1:4 (w/w).

In a further embodiment said inducer is IPTG wherein preferably the concentration of said IPTG said medium is 0.001 to 5 mM, preferably 0.001 to 1 mM, more preferably 0.005 to 1 mM, still more preferably 0.005 to 0.5 mM. In a very preferred embodiment said concentration of IPTG is about 0.01 mM, most preferably 0.01 mM.

In one embodiment said lacI is overexpressed by said bacterial host, wherein said overexpression is caused by $lacI^q$ or lacQ1, preferably by $lacI^q$. In one embodiment said bacterial host comprises said $lacI^q$ gene or said lacQ1 gene, preferably said $lacI^q$ gene on its chromosome. In a further preferred embodiment said bacterial host comprises said $lacI^q$ gene or said lacQ1 gene, preferably said $lacI^q$ gene on a plasmid, preferably on a high copy number plasmid. In a further preferred embodiment said bacterial host comprises said $lacI^q$ gene or said lacQ1 gene, preferably said $lacI^q$ gene on said expression plasmid.

In one embodiment said bacterial host is selected from the group consisting of the strains *E. coli* RB791, *E. coli* DH20 and *E. coli* Y1088. Preferably said bacterial host is *E. coli* RB791.

In one embodiment said bacterial host comprises β-galactosidase activity.

In one embodiment said cultivating and said feeding of said batch culture and said inducing of said promoter is performed at a temperature which is below the optimal growth temperature of said bacterial host. Preferably said temperature is between 23° C. and 35° C., more preferably between 25 and 33° C., even more preferably between 27 and 32° C., still more preferably between 28 and 31° C. Even more preferably said temperature is about 30° C., most preferably said temperature is 30° C.

In one embodiment said cultivating and said feeding of said batch culture is performed at a temperature which is below the optimal growth temperature of said bacterial host, wherein preferably said temperature is between 23° C. and 35° C., more preferably between 25 and 33° C., even more preferably between 27 and 32° C., still more preferably between 28 and 31° C., even more preferably said temperature is about 30° C., most preferably said temperature is 30° C., and said inducing of said promoter is performed at the optimal growth temperature of the bacterial host, preferably at about 37° C.

In one embodiment said cultivating and said feeding of said batch culture and said inducing of said promoter is performed in the absence of an antibiotic.

In a specific embodiment said expression plasmid comprises or alternatively consists of the nucleotide sequence of SEQ ID NO:1, said major carbon source is glycerol, said feeding of said batch culture is performed with a flow rate, wherein said flow rate increases with an exponential coefficient μ, and wherein said exponential coefficient μ is below $μ_{max}$, said inducing of said promoter by co-feeding said batch culture is performed with a constant flow rate, wherein lactose and glycerol are co-fed to the batch culture in a ratio of about 2:1 to about 1:4 (w/w), preferably about 1:1 to about 1:4 (w/w), most preferably about 1:3 (w/w), and wherein said cultivating and feeding of said batch culture and said inducing of said promoter is performed at a temperature between 27 and 32° C., preferably about 30° C., most preferably 30° C.

In a further specific embodiment said expression plasmid comprises or alternatively consists of the nucleotide sequence of SEQ ID NO:30, said major carbon source is glycerol, said feeding of said batch culture is performed with a flow rate, wherein said flow rate increases with an exponential coefficient $\mu$, and wherein said exponential coefficient $\mu$ is below $\mu_{max}$, said inducing of said promoter by co-feeding said batch culture is performed with a constant flow rate, wherein lactose and said major carbon source are co-fed to the batch culture in a ratio of about 2:1 to about 1:4 (w/w), preferably about 1:1 to about 1:4 (w/w), most preferably about 1:3 (w/w), and wherein said cultivating and feeding of said batch culture and said inducing of said promoter is performed at a temperature between 27 and 32° C., preferably about 30° C., most preferably 30° C.

DESCRIPTION OF THE FIGURES

FIG. 1: Fermentation profile with pTac-nSD-Qb-mut (SEQ ID NO:1) in RB791 in 21 culture. Co-feeding during production phase was performed with medium containing 20% glycerol and 20% lactose. Shown are glycerol concentration [g/l] (circles); lactose concentration [g/l] (triangles); β-Gal activity [U/ml*OD=1] (squares) and OD600 (diamonds) plotted against the process time [h].

DETAILED DESCRIPTION OF THE INVENTION

Unless defined otherwise, all technical and scientific terms used herein have the same meanings as commonly understood by one of ordinary skill in the art to which this invention belongs.

"about": within the meaning of the present application the expression about shall have the meaning of +/−10%. For example about 100 shall mean 90 to 110.

"promoter which is inducible by lactose" as used herein refers to a promoter which comprises regulatory elements of the lac operon. Such promoters are repressed by lacI and can be induced by lactose or the synthetic inducer IPTG. The skilled person is aware that induction of a promoter by lactose requires β-galactosidase activity in the bacterial host.

"located directly 3'": a nucleotide sequence N2 which is located directly 3' of another nucleotide sequence N1 refers to a continuous sequence having the conformation 5'-N1-N2-3' wherein N1 and N2 are directly connected and not separated by additional sequence elements.

"sequence stretch": as used herein the term "sequence stretch" refers to a continuous nucleotide sequence which consists of less than 50, preferably less than 20, more preferably less than 10, even more preferably less than 5 nucleotides. In a further preferred embodiment the sequence stretch comprises or alternatively consists of at least one, preferably one, TAA stop codon. In another embodiment the sequence stretch comprises or alternatively consists of at least one, preferably one, TAA and at least one, preferably one, TGA stop codon. In further preferred embodiment the sequence stretch comprises or alternatively consists of SEQ ID NO:32.

"bacterial host": as used herein the term "bacterial host" refers to a bacterial organism which is hosting or capable of hosting an expression plasmid of the invention, wherein "hosting" involves the replication of the expression plasmid and maintenance of the expression plasmid during cell division.

"culture": in the context of the instant invention a "culture" comprises a bacterial host in a medium ("bacterial culture"), wherein typically said medium is supporting the growth of said bacterial host.

"batch culture" as used herein relates to a culture, i.e. a bacterial host in a medium, wherein said culture constitutes a closed system, i.e. typically and preferably no addition or removal of medium takes place during the cultivation time. Therefore, in contrast to a continuous culture, typically and preferably the density of the bacterial host in the batch culture continuously increases with progressing cultivation time. Batch culture does not exclude the addition of compounds required for the control of the process, such as, for example, inducer, oxygen, and alkali or acid to control the pH.

"fed batch culture": as used herein is a culture which is supplied with additional medium comprising a substrate, preferably the major carbon source of the bacterial host (feed or co-feed medium). In the context of the application this process is referred to by the terms "feeding said batch culture" (medium comprises the major carbon source) and "co-feeding said batch culture" (medium comprises the major carbon source and the inducer, preferably lactose). Typically and preferably, no removal of medium except for analytical purposes takes place during cultivation time of a fed batch culture.

"Preculture": a culture, preferably a batch culture, which is used to produce the inoculum for a culture of a large volume, e.g. the culture in which the recombinant capsid protein is produced (production culture). A preculture can be performed in two or more steps, wherein a second preculture is inoculated with a first preculture etc. to produce a sufficiently large inoculum for the production culture. The first and/or subsequent precultures may comprise an antibiotic to improve plasmid stability.

"substrate": as used herein refers to a compound in the culture medium which contributes to the carbon and energy supply of the bacterial host. The terms "substrate" therefore encompasses any compound contained in the medium contributing to the carbon supply of the bacterial host. Typical substrates for bacteria are sugar, starch, glycerol, acetate and any other organic compound which can be metabolized by bacteria. Therefore, the term "substrate" includes the major carbon source but also, for example, lactose.

"Major carbon source" as used herein refers to the compound in the culture medium which contributes most to the carbon and energy supply of the bacterial host during the growth phase. The major carbon source thus is the major substrate of the bacterial host. The major carbon source is typically a sugar such as sucrose or glucose, or glycerol, and preferably glucose or glycerol. Though lactose could in principal act as a major carbon source for a bacterial host, in the context of the instant invention the term "major carbon source" typically and preferably does not include lactose.

Phases of the process of the invention: The process of the invention is characterised by different phases which refer to different physiological conditions of the bacterial host with respect to its growth and the repression/induction status of the expression construct.

"Growth phase": The growth phase is initiated by said cultivating said bacterial host in a medium. The growth phase is preferably characterized by conditions under which the promoter driving the expression of the recombinant capsid protein is repressed and the growth phase is terminated with said inducing said promoter with an inducer. The growth phase can be further divided in a "batch phase" and a "feed phase". Said batch phase is initiated by said cultivating said bacterial host in a medium. The batch phase comprised a "lag phase" during which the bacterial host is not yet growing or growing with a non-exponential rate, typically and preferably a linear rate. The growth phase further comprises an "exponential growth phase" which directly follows the lag phase. No feeding of said culture takes place doting the batch phase, thus the exponential growth phase is terminated by the consumption of the substrate by the bacterial host. The growth phase further comprises a "feed phase" which is directly following the batch phase and which is initiated by said feeding of said batch culture with said major carbon source. The feed phase is characterised by a growth rate of the bacterial host which is directly dependent on the flow rate of the feed medium containing the major carbon source.

"production phase": The growth phase is followed by the production phase which is initiated by said inducing said promoter with an inducer, wherein typically and preferably said feeding of said batch culture with said major carbon source is continued.

"Conditions under which the promoter is repressed": it is to be understood that the repression of a promoter is an equilibrium of formation and dissociation of the repressor-operator complex and that even stringently repressed promoters may show a certain expression rate also in the absence of their inducer. Therefore, as used within the application the term "conditions under which the promoter is repressed" relates to conditions, wherein at the end of the growth phase, i.e. directly before the addition of inducer to the culture, the recombinant capsid protein is expressed to a level which does not exceed a concentration in the medium of 200 mg/l, preferably 150 mg/l, more preferably 100 mg/l, as determined by the HLPC method of Example 17. Most preferably, the concentration of the recombinant protein is below the detection level of said method.

"Inducer": within the meaning of the in invention the term "inducer" relates to any substance which directly or indirectly interacts with an inducible promoter and thereby facilitates expression from said promoter; for example, inducers of "a promoter inducible by lactose", such as the lac or tac promoter, are IPTG, lactose and allolactose.

"Coat protein"/"capsid protein": The term "coat protein" and the interchangeably used term "capsid protein" within this application, refers to a viral protein, preferably a subunit of a natural capsid of a virus, preferably of a RNA bacteriophage, which is capable of being incorporated into a virus capsid or a VLP. For example, the specific gene product of the coat protein gene of RNA bacteriophage Qβ is referred to as "Qβ CP", whereas the "coat proteins" or "capsid proteins" of bacteriophage Qβ comprise the "Qβ CP" as well as the A1 protein.

"Recombinant capsid protein": A capsid protein which is synthesised by a recombinant host cell.

"Polypeptide": As used herein the term "polypeptide" refers to a polymer composed of amino acid residues, generally natural amino acid residues, linked together through peptide bonds. Although a polypeptide may not necessarily be limited in size, the term polypeptide is often used in conjunction with peptide of a size of about ten to about 50 amino acids.

"Protein": As used herein, the term protein refers to a polypeptide generally of a size of above 20, more particularly of above 50 amino acid residues. Proteins generally have a defined three dimensional structure although they do not necessarily need to, and are often referred to as folded, in opposition to peptides and polypeptides which often do not possess a defined three-dimensional structure, but rather can adopt a large number of different conformations, and are referred to as unfolded.

"Recombinant host cell": As used herein, the term "recombinant host cell" refers to a host cell into which one ore more nucleic acid molecules of the invention have been introduced.

"Recombinant VLP": The term "recombinant VLP", as used herein, refers to a VLP that is obtained by a process which comprises at least one step of recombinant DNA technology. The term "VLP recombinantly produced", as used herein, refers to a VLP that is obtained by a process which comprises at least one step of recombinant DNA technology. Thus, the terms "recombinant VLP" and "VLP recombinantly produced" are interchangeably used herein and should have the identical meaning.

"RNA-bacteriophage": As used herein, the term "RNA-bacteriophage" refers to RNA viruses infecting bacteria, preferably to single-stranded positive-sense RNA viruses infecting bacteria.

"Virus-like particle (VLP)": as used herein, the term "virus-like particle" refers to a structure resembling a virus particle or it refers to a non-replicative or non-infectious, preferably a non-replicative and non-infectious virus particle, or it refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. Typically a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA-phage. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of viral capsid or viral-capsid like structure with an inherent repetitive organization, wherein said structure is, typically, spherical or tubular. For example, the capsids of RNA bacteriophages or HBcAgs have a spherical form of icosahedral symmetry.

"Virus-like particle of a RNA bacteriophage": As used herein, the term "virus-like particle of a RNA bacteriophage" refers to a virus-like particle comprising, or preferably consisting essentially of or consisting of coat proteins, mutants or fragments thereof, of a RNA bacteriophage. In addition, virus-like particle of a RNA bacteriophage resembling the structure of a RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. Preferred VLPs derived from RNA bacteriophages exhibit icosahedral symmetry and consist of 180 subunits. A preferred method to render a virus-like particle of a RNA bacteriophage non replicative and/or non-infectious is by genetic manipulation.

one, a, or an: When the terms "one," "a," or "an" are used in this disclosure, they mean "at least one" or "one or more," unless otherwise indicated.

"Sequence identity": The amino acid sequence identity of polypeptides can be determined conventionally using known computer programs such as the Bestfit program. When using Bestfit or any other sequence alignment program, preferably using Bestfit, to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, polypeptides or a fragment thereof disclosed in this invention.

"Sequence homology": The homology of nucleotide sequences can for example be determined by the program blastn which is an implementation of the BLAST algorithm, preferably using the default settings of the software.

"Fragment of a protein", in particular fragment of a recombinant protein or recombinant coat protein, as used herein, is defined as a polypeptide, which is of at least 70%, preferably at least 80%, more preferably at least 90%, even more preferably at least 95% the length of the wild-type recombinant protein, or coat protein, respectively and which preferably retains the capability of forming VLP. Preferably the fragment is obtained by at least one internal deletion, at least one truncation or at least one combination thereof. Further preferably the fragment is obtained by at most 10, at most 9, at most 8, at most 7, at most 6, at most 5, at most 4, at most 3 or at most 2 internal deletions; by at most 10, at most 9, at most 8, at most 7, at most 6, at most 5, at most 4, at most 3 or at most 2 truncations; or by at most 3, preferably at most 2, most preferably by exactly one combination thereof. Most preferably the fragment is obtained by exactly one internal deletion, exactly one truncation or by a combination thereof.

The term "fragment of a recombinant protein" or "fragment of a coat protein" shall further encompass polypeptide, which has at least 80%, preferably 90%, even more preferably 95% amino acid sequence identity with the "fragment of a recombinant protein" or "fragment of a coat protein", respectively, as defined above and which is preferably capable of assembling into a virus-like particle.

The term "mutant recombinant protein" or the term "mutant of a recombinant protein" as interchangeably used in this invention, or the term "mutant coat protein" or the term "mutant of a coat protein", as interchangeably used in this invention, refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

The invention is related to an efficient fermentation process for the production of a VLP of a bacteriophage. The process is improved with respect to yield of the VLP and can be scaled up to a commercial production scale. The process encompasses the expression of recombinant capsid protein of bacteriophages in a bacterial host under conditions which allow the capsid protein to self-assemble into VLPs spontaneously.

Specific examples of VLPs which can be produced by the process of the invention are VLPs of bacteriophages, preferably RNA bacteriophages. In one preferred embodiment of the invention, the virus-like particle of the invention comprises, consists essentially of, or alternatively consists of, recombinant coat proteins, mutants or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; l) bacteriophage PP7 and m) bacteriophage AP205.

In one preferred embodiment of the invention, VLPs are produced comprising coat protein, mutants or fragments thereof, of RNA bacteriophages, wherein the coat protein has an amino acid sequence selected from the group consisting of (a) SEQ ID NO:5. referring to Qβ CP; (b) a mixture of SEQ ID NO:5 and SEQ ID NO:15 (Qβ A1 protein); (c) SEQ ID NO:16 (R17 capsid protein); (d) SEQ ID NO:17 (fr capsid protein); (e) SEQ ID NO:18 (GA capsid protein); (f) SEQ ID NO:19 (SP capsid protein); (g) a mixture of SEQ ID NO:19 and SEQ ID NO:20; (h) SEQ ID NO:21 (MS2 capsid protein); (i) SEQ ID NO:22 (M11 capsid protein); (j) SEQ ID NO:23 (MX1 capsid protein); (k) SEQ ID NO:24 (NL95 capsid protein); (l) SEQ ID NO:25 (f2 capsid protein); (m) SEQ ID NO:26 (PP7 capsid protein); and (n) SEQ ID NO:12 (AP205 capsid protein).

Upon expression in *E. coli*, the N-terminal methionine of Qβ coat protein is usually removed (Stoll, E. et al., J. Biol. Chem. 252:990-993 (1977)). VLP composed of Qβ coat proteins where the N-terminal methionine has not been removed, or VLPs comprising a mixture of Qβ coat proteins where the N-terminal methionine is either cleaved or present are also within the scope of the present invention.

In one preferred embodiment of the invention, the VLP is a mosaic VLP comprising or alternatively consisting of more than one amino acid sequence, preferably two amino acid sequences, of coat proteins, mutants or fragments thereof, of a RNA bacteriophage.

In one very preferred embodiment, the VLP comprises or alternatively consists of two different coat proteins of a RNA bacteriophage, said two coat proteins have an amino acid sequence of SEQ ID NO: 5 and SEQ ID NO:15, or of SEQ ID NO:19 and SEQ ID NO:20.

In preferred embodiments of the present invention, the produced VLP comprises, or alternatively consists essentially of, or alternatively consists of recombinant coat proteins, mutants or fragments thereof, of the RNA-bacteriophage Qβ, fr, AP205 or GA.

In one preferred embodiment, the VLP is a VLP of RNA-phage Qβ. The capsid or virus-like particle of Qβ shows an icosahedral phage-like capsid structure with a diameter of 25 nm and T=3 quasi symmetry. The capsid contains 180 copies of the coat protein, which are linked in covalent pentamers and hexamers by disulfide bridges (Golmohammadi, R. et al., Structure 4:543-5554 (1996)).

Preferred virus-like particles of RNA bacteriophages, in particular of Qβ and fr in accordance of this invention are disclosed in WO 02/056905, the disclosure of which is herewith incorporated by reference in its entirety. Particular Example 18 of WO 02/056905 gave detailed description of preparation of VLP particles from Qβ.

In another preferred embodiment, the VLP is a VLP of RNA bacteriophage AP205. Assembly-competent mutant forms of AP205 VLPs, including AP205 coat protein with the substitution of proline at amino acid 5 to threonine, may also be used in the practice of the invention and leads to other preferred embodiments of the invention. WO 2004/007538 describes, in particular in Example 1 and Example 2, how to obtain VLP comprising AP205 coat proteins, and hereby in particular the expression and the purification thereto. WO 2004/007538 is incorporated herein by way of reference.

In one preferred embodiment, the VLP comprises or consists of a mutant coat protein of a virus, preferably a RNA bacteriophage, wherein the mutant coat protein has been modified by removal of at least one lysine residue by way of substitution and/or by way of deletion. In another preferred embodiment, the VLP of the invention comprises or consists of a mutant coat protein of a virus, preferably a RNA bacteriophage, wherein the mutant coat protein has been modified by addition of at least one lysine residue by way of substitution and/or by way of insertion. The deletion, substitution or addition of at least one lysine residue allows varying the degree of coupling with an antigen.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid.

Qβ mutants, of which exposed lysine residues are replaced by arginines are also encompassed by the present invention. Preferably these mutant coat proteins comprise or alternatively consist of an amino acid sequence selected from the group of a) Qβ-240 (SEQ ID NO:7, Lys13→Arg); b) Qβ-243 (SEQ ID NO:8, Asn10→Lys); c) Qβ-250 (SEQ ID NO:9, Lys2→Arg); d) Qβ-251 (SEQ ID NO:10, Lys16→Arg); and e) Qβ-259 (SEQ ID NO:11, Lys2→Arg, Lys16→Arg). The construction, expression and purification of the above indicated Qβ mutant coat proteins, mutant Qβ coat protein VLPs and capsids, respectively, are described in WO02/056905. In particular is hereby referred to Example 18 of above mentioned application.

In a further preferred embodiment the recombinant capsid protein is a capsid protein of bacteriophage AP205 having the amino acid sequence depicted in SEQ ID NO:12 or a mutation thereof, which is capable of forming a VLP, for example the proteins AP205P5T (SEQ ID NO:13) or AP205 N14D (SEQ ID NO:14.).

In a very preferred embodiment said recombinant capsid protein is composed of the 133 amino acid coat protein C of E. coli RNA bacteriophage Qβ comprising or preferably consisting of the amino acid sequence depicted in SEQ ID NO:5, wherein preferably said recombinant capsid protein is capable of forming a VLP by self-assembly.

In one embodiment, the expression construct comprises a first stop codon and a second stop codon, wherein said first stop codon is located directly 3' of said first nucleotide sequence and wherein said second stop codon is located directly 3' of said first stop codon, and wherein at least one of said first or second stop codon is TAA. For example, plasmid pTac-nSDAP205 (SEQ ID NO:30) comprises the naturally occurring TAA stop codon as a first stop codon and an additional TGA stop codon directly 3' of the first stop codon.

In a preferred embodiment the expression construct comprises a first nucleotide sequence and a second nucleotide sequence, wherein said first nucleotide sequence is encoding a recombinant capsid protein, preferably Qβ CP, or a mutant or fragment thereof, most preferably SEQ ID NO:5, and wherein said second nucleotide sequence is encoding any other protein, preferably the Qβ A1 protein or a mutant or fragment thereof, most preferably SEQ ID NO:15, and wherein said first and said second nucleotide sequence are separated by exactly one sequence stretch comprising at least one TAA stop codon. In one embodiment said TAA stop codon is generated by replacing the naturally occurring stop codon, preferably TGA by the sequence TAA. Alternatively and more preferably said TAA stop codon is generated by replacing the naturally occurring stop codon, preferably TGA by the sequence TAATGA (SEQ ID NO:32).

For example, the region of Qβ gene C corresponds to the NCBI GenBank Acc. No. M99039 (nucleotides 46-1062). Gene C contains a first nucleotide sequence encoding the 133-amino acid Qβ coat protein (SEQ ID NO:5) and a second nucleotide sequence encoding the 329-amino acid read through protein A1 (SEQ ID NO:15). Nucleotides 1-399 of SEQ ID NO:6 (nucleotides 46-444 of NCBI GenBank Acc. No. M99039) correspond to said first nucleotide sequence encoding the 133-amino acid Qβ CP, Nucleotides 400 to 402 of SEQ ID NO:6 correspond to the strong TAA stop codon and nucleotides 403 to 405 of SEQ ID NO:6 to the leaky TGA stop codon, which is followed by said second nucleotide sequence (Qβ A1). Surprisingly, it was found that the presence of the nucleotide sequence relating to A1 in the expression construct results in higher RNA stability and, thus, in improved yield of Qβ CP and VLP as compared to a construct wherein the A1 sequence is deleted.

The expression of a recombinant protein can significantly reduce the growth rate of the bacterial host due to toxic effects of the accumulating protein and due to the metabolic burden caused by the protein synthesis. In particular cell lysis and low plasmid retention may occur. Inducible promoters provide for the possibility to separate the growth phase from the production phase of a fermentation process. Inducible promoters are repressed by a repressor molecule during the growth phase of the bacterial host and are induced by exposing the bacterial host to inductive conditions during the production phase. Inducible promoters therefore allow the bacterial host to grow fast, preferably exponentially during the growth phase and to reach high cell densities. Thus, inducible promoters provide for high yield of the expression product at the end of the production phase. Therefore, the usage of inducible promoters for the expression of recombinant protein is preferred.

A well known example for an inducible promoter is the lac promoter which forms part of the lac operon and which can be induced by addition of lactose or the strong synthetic inducer isopropylthio-β-D-galactosid (IPTG) to the growth medium of the bacterial host. Donavan et al. 2000 (Can. J. Microbiol 46:532-541) report on an improved process for the expression of a monoclonal antibody fragment under the control of the lac promoter. Further examples of inducible promoters are provided in table 1 of Makrides 1996 (Microbiological Reviews, p. 512-538).

A typical drawback of expression systems based on inducible promoters is the "leakiness" of the promoter, meaning that the promoter is only insufficiently repressed and causes a certain expression rate of the recombinant protein during the growth phase. This typically leads to a reduced cell density or to plasmid instability and, as a consequence, to reduced yield of the recombinant protein Makrides 1996 (Microbiological Reviews, p. 512-538). An example of a promoter which is prone to insufficient repression is the VHb promoter which is repressed under high oxygen conditions and induced upon oxygen depletion.

For the purpose of the invention promoters arc preferred which are stringently repressed. In one embodiment the promoter is repressed by the repressor lacI. Examples of such promoters are disclosed in Makrides 1996 (Microbiol. Rev. 60:512-538), Goldstein & Doi 1995 (Biotechnology Annual Review 1:105-128), Hannig & Makrides 1998 (TIBTECH 16:54-60) and Stevens 2000 (Structures 8, R177-R185). In a preferred embodiment the promoter is inducible by lactose, more preferably it is selected from the group consisting of lac, lacUV5, tac, trc, $P_{syn}lpp^a$, lpp-lac, T7-lac, T3-lac, and T5-lac. Especially preferred for the purpose of the invention is the tac promoter (SEQ ID NO:2) or a mutation or variant thereof. Within the scope of the invention are mutants or truncated or deleted variants of the tac promoter having a sequence homology with SEQ ID NO:2 which is at least 50%, 60%, 70%, 80, 90, or 95%, preferably 98 to 100%, most preferably 99%. Wherein the promoter strength of such mutated truncated or deleted variant is comparable to that of the promoter of SEQ ID NO:2. The skilled person will be able to determine the promoter strength of a given sequence by comparative expression studies using standard methods. In a specific embodiment of the invention the promoter driving the expression of the recombinant capsid protein comprises or alternatively consists of SEQ ID NO:2. The tac promoter is a fusion product of the −10 region of the lacUV5 promoter and the −35 region of the tip promoter and combines the high transcription efficiency of trp with the regulatory elements of the lac promoter (de Boer et al. 1983, PNAS 80:21-25; Amann et al. 1983 Gene 25:167-178). It provides for sufficiently high expression rates and high protein yield while avoiding the formation of insoluble or incorrectly folded recombinant protein which may occur with stronger promoters, such as the T7 promoter. The lre and the tic promote: are mutated versions of the tac promoter (Brosius et al. 1985, The Journal of Biological Chemistry 260(6): 3539-3541). In a further preferred embodiment the promoter is selected from the group consisting of tic, trc and tac.

For the construction of an expression construct for the purpose of the invention the promoter is operably linked to said first nucleotide sequence encoding the recombinant capsid protein via a ribosome binding site (Shine-Dalgarno sequence, SD), typically comprising an ATG start codon at its 3' end. Suitable Shine-Dalgarno sequences for the purpose of the invention are well known in the art (Dalbøge et al. 1988, DNA 7(6):399-405; Ringquist et al. 1992, Mol. Micr. 6:1219-1229). In one embodiment of the invention the expression construct comprises the SD sequence of Dalbøge et al. 1988 (DNA 7(6):399-405) which is depicted in SEQ ID NO:4. In another, preferred, embodiment the expression construct comprises a Shine-Dalgarno sequence of Ringquist et al. 1992 (Mol. Micr. 6:1219-1229, SEQ ID NO:3, nSD). Surprisingly, it was found that SEQ ID NO:3 is particularly suited for the purpose of the invention because it results in improved expression levels and improved yield of recombinant capsid protein. SEQ ID NO:3 is especially suited to enhance the expression of AP205 capsid protein. In a preferred embodiment of the invention the expression construct comprises a Shine-Dalgarno sequence selected form the group consisting of SEQ ID NO:3 and SEQ ID NO:4, preferably said Shine-Dalgarno sequence is SEQ ID NO:3.

Transcriptional terminators are functional elements of expression constructs. The skilled person will be able to choose a suitable terminator sequence form a wide range of sources. In a preferred embodiment of the invention said expression construct comprises a terminator sequence, wherein preferably said terminator sequence is operably linked to said first nucleotide sequence, wherein further preferably said terminator sequence is the rRNB terminator sequence, most preferably SEQ ID NO:28.

For the purpose of plasmid selection the skilled person will typically use an antibiotic resistance marker gene. Examples of antibiotic resistance genes which are widely used in the art and which are suitable for the purpose of the invention are resistance genes against the antibiotics ampicillin, tetracyclin and kanamycin. The use of kanamycin as a selective agent in the frame of a process for the production of a VLP is generally preferred because of the lower allergenic potential of kanamycin as compared to alternative antibiotics and because of the lower safety concerns resulting thereof for the use of the VLP as a vaccine. Furthermore, kanamycin provides better plasmid retention as compared to alternative antibiotics such as ampicillin. The kanamycin 3'-phosphotransferase gene (SEQ ID NO:29) which is derived from the transposon Tn903 is therefore a particularly useful selectable marker gene.

The addition of antibiotics to the medium is generally undesirable in a commercial production process for cost and safety reasons. In the context of the invention antibiotics, preferably kanamycin, are typically and preferably used for the selection of the expression strain. Media used in the production process are essentially free of antibiotics, in particular kanamycin. However, addition of an antibiotic to precultures used to produce the inoculum for the production culture can improve plasmid retention throughout the process (Example 10).

The skilled person will create expression plasmids comprising expression constructs which are useful for the production of VLPs of bacteriophages by combining the genetic elements described above applying standard methods of molecular biology. Particularly useful expression plasmids for the purpose of the invention are pTac-nSDQb-mut (SEQ ID NO:1) for the production of Qβ VLP and pTac-nS-DAP205 (SEQ ID NO:30) for the production of AP205 VLP. The construction of these specific expression plasmids is described in detail in the Examples section.

The expression plasmids are transformed to a bacterial expression host by any method known in the art, preferably by electroporation. Individual clones of the host comprising the expression plasmid are selected for maximal expression of the recombinant capsid protein by SDS-PAGE after cell lysis. Selected clones of the expression host comprising the expression plasmid can be stored as frozen glycerol cultures.

Said bacterial host can be chosen from any bacterial strain capable of replicating and maintaining said expression plasmid during cell division. Preferred bacterial hosts are Escherichia coli strains having the specific features described in the following sections.

The repression of the promoter is improved by overexpression of the repressor by the bacterial host. In one embodiment said cultivating of said bacterial host is performed in batch culture and under conditions under which said promoter is repressed by lacI. In a preferred embodiment the gene causing overexpression of said lacI in said bacterial host is located on a plasmid, preferably on said expression plasmid. Alternatively, said gene is located on a separate plasmid contained in said bacterial host, wherein said separate plasmid preferably is a high copy number plasmid. Alternatively, and most preferably said gene is located on the chromosome of said bacterial host.

One example of a gene causing overexpression of lacI is $lacI^q$ (Menzella et al. 2003, Biotechnology and Bioengineering 82(7)809-817) which is a single CG to TA change at −35 of the promoter region of lacI which causes a 10 fold increase in LacI expression. A further example is lacIQ1 (Glascock & Weickert 1998, Gene 223(1-2):221-231). Improved repression of the promoter during the growth phase results in improved plasmid retention and higher cell density and, ultimately, in improved protein yield. For example, bacterial strains comprising the $lacI^q$ gene overexpress the lacI repressor molecule and therefore prevent formation of the recombinant protein during the growth phase more efficiently than strains comprising the wildtype gene. In a preferred embodiment the gene causing overexpression of said lacI is lacIQ1 or lacI$^q$, preferably lacI$^q$. In a specifically preferred embodiment said bacterial host comprises the lacI$^q$ gene on its chromosome.

In one embodiment said inducing of said promoter is performed with an inducer, wherein said inducer is preferably selected from IPTG and lactose, most preferably said inducer is lactose. Upon exposure of the bacterial host to an inducer, the repressor is inactivated and the promoter becomes active. Addition of the strong inducer IPTG to the culture medium results in an immediate increase of the expression rate of the recombinant protein to a high level because IPTG directly enters the cells by diffusion and binds and inactivates the active repressor lacI. Inactivated lacI repressor molecules dissociates from the operator and allow high level transcription from the promoter. IPTG is not metabolized by the cell and the transcription continues with high rates until other metabolic parameters become limiting.

As mentioned before, high expression rates may lead to the formation of insoluble recombinant protein which is not capable of forming a 'VLP' by self-assembly. Induction of protein expression with high concentrations of IPTG is particularly prone to the formation of insoluble protein. Therefore, induction of the promoter is preferably achieved by the addition of IPTG in concentrations which are below the concentration which causes the expression to occur at its maximum rate (Kopetzki et al. 1989, Mol Gen Genet 216:149-155).

In a preferred embodiment said inducing of said promoter is performed with IPTG, wherein the concentration of said IPTG in said medium is about 0.001 to 5 mM, preferably 0.001 to 1 mM, more preferably 0.005 to 1 mM, still more preferably 0.005 to 0.5 mM. In a specifically preferred embodiment the concentration of said IPTG is about 0.01 mM, most preferably 0.01 mM.

Alternatively, induction of the promoter is achieved by the addition of lactose. Induction of recombinant protein expression with lactose requires that the bacterial host is capable of taking up lactose from the medium, e.g. by Lac permease and that it comprises β-galactosidase activity. The Lac permease dependent uptake of lactose into the cells follows a slower kinetic than the uptake of IPTG by diffusion. Furthermore, lactose does not directly interact with the lac operon but is converted by β-galactosidase to allolactose (1-6-O-β-galactopyranosyl-D-glucose) which is the actual inducer of the promoter. Induction of recombinant protein expression by the addition of lactose is advantageous because it avoids the immediate increase of the expression rate to a maximum level upon addition of the inducer and, thus, it reduces the risk of the formation of insoluble protein.

Allolactose is metabolised by the bacterial host during the production phase and contributes carbon and metabolic energy to the bacterial metabolism. This may further contribute to improved protein yield as compared to induction with IPTG. Furthermore, induction by lactose allows to a certain extend the control of the expression rate of the recombinant protein during the production phase via the lactose concentration in the medium. Induction by lactose is further preferred in a pharmaceutical production process because IPTG is expensive and is believed to be toxic. Its removal needs to be demonstrated at the end of a the production process.

In a preferred embodiment said inducing of said promoter is performed by the addition of lactose to said batch culture, wherein preferably said bacterial host is capable of taking up lactose from the medium and wherein further preferably said bacterial host comprises β-galactosidase activity. Such bacteria strains can, for example, be obtained from strain collections such as AITC (www.atcc.org). In a preferred embodiment, said bacterial host is an *E. coli* strain, preferably an *E. coli* strain selected from the group consisting of RB791, DH20, Y1088, W3110 and MG1655. Most preferably, said bacterial host is *E. coli* RB79L In a still more preferred embodiment said promoter is the tac promoter or mutant or variant thereof and said bacterial host is an *E. coli* strain which further comprises a gene causing overexpression of a repressor of the lac promoter, wherein said gene preferably is lacI$^q$. The pH of the culture medium of the bacterial host can be controlled during the fermentation process and regulated by the addition of acidic or alkaline solutions using methods which are well known in the art. In one embodiment, said cultivating of said bacterial host and said feeding of said hatch culture is performed under conditions, wherein the pH of the medium is controlled. In a preferred embodiment said pH is between 5.5 and 8.0, more preferably between 6.5 and 7.5, even more preferably between 6.7 and 7.0 and most preferably said pH of said medium is 6.8. Said pH of said medium may be kept constant during the process or it may follow a certain profile during the different phases of the process within the pH ranges specified above. In a preferred embodiment said pH is kept constant at a value of 6.7 to 7.0, preferably said pH it is kept constant at 6.8.

The process of the invention comprises a growth phase, wherein said growth phase comprises a batch and a feed phase, wherein said growth phase and simultaneously said batch phase are initiated by said cultivating said bacterial host and wherein said feed phase is initiated by said feeding of said batch culture with said major carbon source.

The oxidative capacity of bacteria cells is limited and high concentrations of the substrate may cause the formation of reduced products like acetate, which may lead to undesired acidification of the medium and to reduced growth of the bacteria. Therefore, the bacterial host is grown in a fed-batch culture on a minimum medium with a limited quantity of substrate. In one embodiment said cultivating of said bacterial host is performed in a medium comprising said major carbon source, wherein said medium preferably is a minimal medium, preferably a chemically defined minimal medium. Most preferably said medium is R27 medium as described in Example 5.

At the end of the batch phase, when the substrate contained in the medium is almost exhausted, medium containing the major carbon source (feed medium) is fed to said batch culture at the same rate as the desired growth rate of the bacterial host, i.e. the growth rate of the bacterial host is limited by the feed rate of the substrate. It is understood by the skilled person that the decisive parameter is the actual mass flow of the substrate, preferably the major carbon source, and other nutrients required to maintain growth. Since in practice a constant composition of the feed medium can be assumed, the flow rate refers to the volume flow of the medium. The same consideration applies to the co-feed medium (see below).

Therefore, in one embodiment said feeding of said batch culture with said major carbon source is performed with a flow rate, wherein said flow rate is limiting the growth rate of said bacterial host.

During the feed phase the growth rate can be freely selected in a wide range nearly up to the maximum growth rate ($\mu_{max}$) if no inhibition occurs. The actual value of $\mu_{max}$ is highly dependent on the bacterial strain, the expression construct and the growth conditions. The skilled person will understand that the determination of $\mu_{max}$ is performed under conditions under which the promoter is repressed.

For a given experimental set up, $\mu$ can be determined from the growth curve of the culture by plotting biomass concentration (x) as determined by $OD_{600}$ or cell wet weight (CWW) against the cultivation time and determining the exponential growth coefficient $\mu$ based on the equation $x=x_0 e^{\mu t}$. The actual value of $\mu_{max}$ is determined as the growth rate $\mu$ of an exponentially growing batch culture in the beginning of the batch phase when no substrate limitation occurs, i.e. without supply of additional medium by feeding. The growth rate $\mu$ can be determined by computing the ratio of the difference between natural logarithm of the total biomass $X_2$ measured at time $t_2$ and natural logarithm of the total biomass $X_1$ measured at time $t_1$ to the time difference $(t_2-t_1)$: $\mu=(\ln X_2-\ln X_1)/(t_2-t_1)$.

Fed-batch culture allows the maintenance of a constant growth rate ($\mu$). In a preferred embodiment the substrate, preferably the major carbon source, is fed during the feed phase according to the exponential increase of the biomass (x). If during the feed phase the substrate is supplied at the same rate it is consumed, the culture is in a quasi steady state, analogous to the cultivation in a continuous culture. Because biomass formation and substrate consumption are correlated over the substrate-referred yield coefficient $Y_{x/s}$ (biomass [g]/substrate [g]), the substrate quantity (s) per time unit (t) to be supplied is calculated according to the formula $ds/dt=\mu/Y_{x/s} \; x_{0\;tot} \; e^{\mu t}$, wherein $x_{0\;tot}$ is the total biomass at feed start.

Therefore, in as preferred embodiment said feeding of said batch culture with said major carbon source is performed with a flow rate, wherein said flow rate increases with an exponential coefficient $\mu$, and wherein preferably said exponential coefficient $\mu$ is below $\mu$max. Thus, the growth rate of said bacterial host during the feed phase is set to a value which is below $\mu_{max}$. In a preferred embodiment said exponential coefficient $\mu$ is about 30% to 70%, most preferably about 50% of $\mu_{max}$. In a specific embodiment of the invention $\mu$ is set to an absolute value of 0.15 to 0.45 $h^{-1}$, more preferably 0.25 to 0.35 $h^{-1}$, most preferably $\mu$ is 0.3 $h^{-1}$, provided that the set up of the process is such, that these values are below $\mu_{max}$.

Bacteria are able to utilise a wide range of different substrates. For the purpose of the invention, preferred major carbon sources are glucose and glycerol, preferably glycerol. Although the maximum specific growth rate ($\mu_{max}$) of the expression host which can be achieved may be higher with glucose than with glycerol, glycerol causes less acetate formation and provides higher biomass yield per substrate ($Y_{x/s}$) and, ultimately, higher yield of the recombinant protein. Furthermore, the handling of the liquid substrate glycerol is easier than that of solid carbon sources like glucose which need to be dissolved in a separate process step.

As mentioned before, plasmid retention, i.e. the maintenance of the expression plasmid in the bacterial host during the fermentation process, is essential for optimal yield of the recombinant protein. Plasmid retention can be assessed by spreading bacteria cells on a solid medium to form single colonies and testing individual colonies for their antibiotic resistance. For example, a plasmid retention of 100% means that 100 out of 100 tested colonies comprise the specific antibiotic resistance which conferred by the expression plasmid. For the purpose of the invention plasmid retention at the end of the fermentation process is more than 80%, preferably more than 90%, more preferably more than 95%, even more preferably more than 97% and most preferably 100%.

The optimal growth temperature of a bacterial strain is the temperature at which it reaches its highest maximal growth rate ($\mu_{max}$). Under otherwise not limiting conditions for most *E. coli* strains this temperature is about 37° C. However, growth of the bacterial strain comprising the expression construct at the optimal growth temperature and in the absence of a selective antibiotic may favour the loss of the expression plasmid, whereas plasmid retention is generally improved when the expression strain is grown at lower temperature. Although the maximum growth rate of the expression strain is lower when the strain is grown at temperatures below its optimal growth temperature as compared to growth at the optimal growth temperature, the yield of recombinant protein may be equal or even better at the lower temperature due to improved plasmid retention.

In one embodiment of the invention, said cultivating of said bacterial host and/or said feeding of said batch culture with said major carbon source and/or said inducing said promoter with an inducer is therefore performed at a temperature below the optimal growth temperature of said bacterial host. In a preferred embodiment said temperature is between 20 and 37° C., preferably between 23 and 35° C., more preferably between 25 and 33° C., even more preferably between 27 and 32° C., still more preferably between 28 and 31° C. Still more preferably said temperature is about 30° C., most preferably said temperature is 30° C.

The process of the invention comprises a production phase, wherein said production phase is initiated by said inducing said promoter with an inducer. The time point for the initiation of said production phase can be determined based on cultivation time and/or growth parameters.

The growth of the bacterial host during the fermentation process can be assessed by determining the optical density at 600 nm ($OD_{600}$), the cell wet weight (CWW [g/l]) and the cell dry weight (CDW [g/l]). These parameters can be used to define the optimal time point for the start of the production phase by addition of the inducer, preferably lactose, to the medium. It is apparent for the skilled person, that on one hand higher CWW at the beginning of the production phase can be achieved by an extended feed phase and may lead to improved yield of the recombinant protein but that on the other hand over-aged cultures may show insufficient protein expression. The optimal time point for the beginning of the production phase, which is initiated by said inducing of said promoter with an inducer, therefore needs to be determined for the specific production conditions. For example, for expression of Qβ CP in *E. coli* RB791 in a total volume of 2 l, induction is started after ca. 14 h., when $OD_{600}$ has reached about 48 to 60. Surprisingly, similar parameters were found for the same process in a 50 l scale, where induction start is also after ca. 14 h when $OD_{600}$ has reached about 50.

Therefore, in one embodiment of the invention, said inducing of said promoter with said inducer is performed 10 h to 16 h after the beginning of said growth phase, preferably after 12 h to 15 h, more preferably after 13 h to 15 h, most preferably after about 14 h, wherein preferably said inducing of said promoter with said inducer is performed when the $OD_{600}$ has reached about 40 to 60, preferably about 50.

In a further embodiment, said inducing of said promoter with said inducer is performed after an extended feed phase, wherein preferably said inducing of said promoter with said inducer is performed 14 h to 20 h after the beginning of said cultivating of said bacterial host in a medium, preferably after 15 h to 18 h, more preferably after 16 h to 17 h, most preferably after about 16.5 h, wherein preferably said inducing of said promoter with said inducer is performed when the $OD_{600}$ has reached about 80 to 90, preferably about 85.

In one embodiment of the invention said inducing of said promoter with said inducer is performed when the $OD_{600}$ reached a value of 25 to 60, preferably 25 to 55, more preferably 30 to 50, most preferably 30 to 40. In a specifically preferred embodiment said inducing of said promoter with said inducer is performed when $OD_{600}$ is 35.

In another embodiment of the invention said inducing of said promoter with said inducer is performed after an extended feed phase, when the $OD_{600}$ reached a value of 60 to 120, preferably 70 to 110, more preferably 80 to 100, most preferably 80 to 90. In a specifically preferred embodiment the induction is started after and an extended feed phase when $OD_{600}$ is about 85, preferably 85.

Induction with IPTG:

In one embodiment of the invention said inducing of said promoter with an inducer is achieved by the addition of IPTG, wherein preferably said feeding of the culture with the major carbon source is continued. Since IPTG is not metabolized by the bacterial host, induction can be achieve by a single addition of IPTG to the desired concentration. Alternatively, induction can be achieved by a continuous flow of IPTG to the culture. In a preferred embodiment induction is performed by addition of IPTG in a single addition or a continuous flow, wherein said feeding of the batch culture with the major carbon source is continued with a constant or an increasing flow rate of said major carbon source exponentially increasing flow rate of the major carbon source.

Induction with Lactose:

As described above, the induction of protein expression can alternatively be achieved by the addition of lactose to the culture medium. In one embodiment of the invention, at the beginning of the production phase the exponential feed of the substrate is interrupted and the culture is supplied with a constant flow of induction medium containing 100 to 300 g/l, preferably 100 g/l lactose as the sole carbon source (lactose feed medium). Preferably, the constant flow rate of lactose equals approximately the flow rate of the substrate at the end of the feed phase.

In a preferred embodiment of the invention said inducing of said promoter with an inducer is achieved by the addition of lactose, wherein preferably said lactose is fed to said batch culture in a continuous flow during and wherein preferably said feeding of said batch culture with said major carbon source is not continued.

Upon addition of lactose to the culture, the β-galactosidase activity increases, lactose is converted to allolactose which induces the tac promoter and the expression of the recombinant capsid is initiated. In parallel, allolactose is further metabolised and contributes to the energy supply for the bacterial host. The equilibrium of the feeding rate of the induction medium and the lactose consumption by the cells thus determines the expression rate. The enzymatic reactions involved in this cascade allow to control the process in such a way that the formation of inclusion bodies is minimised. The progress of induction process can be monitored by determining the β-galactosidase activity in the culture, e.g. by a β-Gal Assay Kit (Invitrogen, K1455-01).

In a more preferred embodiment of the invention said inducing of said promoter with an inducer is achieved by the addition of lactose, wherein preferably said lactose is ted to said batch culture in a continuous flow during and wherein preferably said feeding of said batch culture with said major carbon source is continued.

Discontinuous Addition of Inducer:

Said inducer can be added to the culture discontinuously by a single addition at the beginning of the production phase or by a few subsequent additions during the production phase. Discontinuous addition of the inducer, especially by a single addition is particularly suited when the inducer is IPTG since IPTG is not metabolized by the bacterial host. Therefore, typically and preferably no replacement of metabolised IPTG is necessary during the production phase. In one embodiment said inducing of said promoter with an inducer is performed by the addition of said inducer, preferably IPTG or lactose, most preferably IPTG, to said medium, wherein said inducer is added to about its final concentration at once by a single addition at the beginning of the production phase, wherein preferably said feeding of said batch culture with said major carbon source is continued. In a preferred embodiment said inducing of said promoter with an inducer is performed by the addition of IPTG to said medium, wherein said IPTG is added to about its final concentration at once by a single addition, wherein preferably said feeding of said batch culture with said major carbon source is continued. Alternatively, said inducing of said promoter with an inducer is performed by the addition of said inducer, preferably IPTG or lactose, most preferably lactose, to said medium, wherein said addition is performed in several steps, preferably in 1 to 5, more preferably in 2 to 4, most preferably in 3 steps during the production phase, wherein preferably said feeding of said batch culture with said major carbon source is continued.

Continuous Addition (Feeding) of Inducer:

Preferably, said inducer is added to the medium in a continuous flow, preferably throughout the production phase. The continuous addition of the inducer is particularly suited for lactose, since lactose is metabolised by the bacterial host and therefore a continuous addition of lactose during the production phase allows to maintain a lactose concentration in the medium which allows for efficient induction of the promoter. In a preferred embodiment, said inducing of said promoter with are inducer is performed by feeding said batch culture with said inducer, wherein preferably said inducer is IPTG or lactose, most preferably lactose, and wherein said feeding is performed in a continuous flow, wherein further preferably said feeding is performed throughout the production phase.

Co-Feeding of Inducer and Major Carton Source:

The expression of the recombinant protein is an energy demanding process. To prevent yield loss which might be caused by the excessive consumption of the inducer by the bacterial host and low expression rates resulting thereof, the culture can be additionally supplemented with substrate, preferably the major carbon source, during the production phase, wherein the flow rate of inducer and/or the major carbon source is constant or increasing, preferably constant. When during the production phase the culture is supplemented with substrate at an increasing flow rate, the flow rate is preferably increasing with an exponential rate.

Co-Feeding with Constant Flow Rate:

In a preferred embodiment said inducing of said promoter with an inducer is performed by co-feeding said batch culture with said inducer and said major carbon source, wherein said inducer is preferably IPTG or lactose, most preferably lactose, and wherein said major carbon source is glucose or glycerol, preferably glycerol, wherein said inducer, preferably lactose and said major carbon source, preferably glycerol are co-fed to said batch culture at a flow rate, wherein said flow rate is preferably about constant. In a further preferred embodiment said flow rate is chosen to allow feeding of said major carbon source to said batch culture at about the same rate as at the end of the growth phase. In a still further preferred embodiment said inducer, preferably lactose, and said major carbon source, preferably glycerol, are contained in the same medium (co-feed medium). In a further preferred embodiment said co-feed medium is fed to said batch culture with a flow rate, wherein said flow rate is preferably about constant, and wherein further preferably said flow rate is chosen to allow feeding of said major carbon source to said batch culture at about the same rate as at the end of the growth phase. In a very preferred embodiment said inducer is lactose and said major carbon source is glycerol, wherein said lactose and said glycerol are co-fed to said batch culture in a ratio of about 2:1 to 1:4 (w/w).

In a further preferred embodiment of the invention lactose and said major carbon source, preferably glycerol, are co-fed to said batch culture in a ration of 0:1 to 1:0 (w/w), preferably about 2:1 to about 1:4 (w/w), more preferably about 1:1 to 1:3 (w/w), most preferably the ratio is about 1:3 (w/w). In a preferred embodiment the ratio of lactose and the major carbon source, preferably glycerol, is 1:1 (w/w). In another preferred embodiment the ratio of lactose and the major carbon source, preferably glycerol, is 1:3 (w/w). In a more preferred embodiment said co-feed medium comprises ca. 200 g/l lactose and ca. 200 g/l glycerol. In a still more preferred embodiment the co-feed medium comprises ca. 100 g/l lactose and ca. 300 g/l glycerol.

Co-Feeding with Increasing Flow Rate:

Alternatively, said inducing of said promoter with an inducer is performed by co-feeding said batch culture with said inducer and said major carbon source, wherein said inducer is preferably IPTG or lactose, most preferably lactose, and wherein said major carbon source is glucose or glycerol, preferably glycerol, wherein said inducer, preferably lactose and said major carbon source, preferably glycerol are co-fed to said batch culture at a flow rate, wherein said flow rate is increasing, wherein said flow rate may increase with a linear or with an exponential characteristic, wherein preferably the initial flow rate is chosen to to allow feeding of said major carbon source to said batch culture at about the same rate as at the end of the growth phase.

Further alternatively said inducing of said promoter with an inducer is performed by co-feeding said batch culture with said inducer and said major carbon source, wherein said inducer is preferably IPTG or lactose, most preferably lactose, and wherein said major carbon source is glucose or glycerol, preferably glycerol, wherein said inducer, preferably lactose is fed to said batch culture at a first flow rate, and wherein said major carbon source, preferably glycerol is fed to said batch culture at a second flow rate, wherein said first flow rate is constant or increasing, preferably constant, and wherein said second flow rate is constant or increasing, preferably increasing, wherein preferably the initial value of said second flow rate is chosen to to allow feeding of said major carbon source to said batch culture at about the same rate as at the end of the growth phase. In a very preferred embodiment said inducer is lactose and said major carbon source is glycerol, wherein said lactose and said glycerol are co-fed to said batch culture in a ratio of about 2:1 to 1:4 (w/w).

The growth of the bacterial host as determined by CDW, CWW or $OD_{600}$ continues during the production phase at a growth rate which is lower than that during the growth phase and which is decreasing with the process time. In a further embodiment of the invention, said inducing said promoter with an inducer is performed by co-feeding said inducer, preferably lactose and said major carbon source, preferably glycerol, to said batch culture with an increasing flow rate, preferably with a flow rate wherein the incremental increase of the flow rate is adapted to the actual growth rate of the culture. In a further preferred embodiment said inducer, preferably lactose, and said major carbon source, preferably glycerol, are contained in the same medium (co-feed medium), wherein preferably the ratio between lactose and glycerol in said medium (co-feed medium) ranges from about 0:1 to 1:0 (w/w), preferably about 2:1 to about 1:4 (w/w), more preferably about 1:1 to 1:3 (w/w), most preferably the ratio is about 1:3 (w/w). In a preferred embodiment the ratio of lactose and the major carbon source, preferably glycerol, is 1:1 (w/w). In another preferred embodiment the ratio of lactose and the major carbon source, preferably glycerol, is 1:3 (w/w). In a more preferred embodiment said medium (co-feed medium) comprises ca. 200 g/l lactose and ca. 200 g/l glycerol. In a still more preferred embodiment the induction medium comprises ca. 100 g/l lactose and ca. 300 g/l glycerol.

In one embodiment of the invention said inducing of said promoter with an inducer is performed by co-feeding said inducer, preferably lactose and said major carbon source, preferably glycerol to said batch culture, wherein said inducer, preferably lactose and said major carbon source, preferably glycerol are contained in separate media which are separately fed to said culture.

At the end of the production phase the cells are harvested by centrifugation. Typically, cells are harvested about 5 h after induction start, when a final $OD_{600}$ of 90 to 130 is reached. Further extension of the production phase leads to higher $OD_{600}$ and CWW values and therefore to further improved yield of the expression construct.

Harvested cells may be suspended in a storage buffer and stored at −80° C. for further processing.

The total protein content of the cells is determined after cell lysis by SDS PAGE or LDS PAGE and comparison with a protein standard. The content of soluble protein is determined by HPLC. The identity of the expressed capsid protein is determined by western blotting. The concentration of assembled VLPs can be analysed by size exclusion chromatography (Example 18). VLP can preparatively be purified from lysed cells by chromatographic methods.

Scale-up of the process of the invention to large volumes is possible with only minor adaptations. The invention encompasses culture volumes in the range of 100 ml up to 6000 l. Preferred culture volumes are 40 to 100 l, most preferably about 50 l. It is apparent for the skilled person that larger culture volumes in particular require larger volumes of the preculture which is used for inoculation. For example, a preculture may be performed in two ore more steps with increasing preculture volume. To ensure plasmid retention in large culture volumes, the precultures which are used as inoculum may contain an antibiotic to maintain selection pressure. The skilled person is aware that plasmid retention can further be improved by reducing the number of generations which is necessary to reach the desired final cell density. Therefore, it is advantageous to inoculate the precultures and the batch cultures with high cell densities. In a preferred embodiment the initial $OD_{600}$ of the preculture is 0.1 to 0.4, preferably about 0.3.

In one embodiment, prior to said cultivation step, said process further comprises the step of introducing said bacterial host into a medium, wherein said introducing is performed with an inoculum, wherein said inoculum is produced in a preculture process comprising the step of growing said bacterial host in a medium comprising an antibiotic, preferably kanamycin. More preferably, said pre-culture process comprises the steps of growing said bacterial host in a first medium comprising an antibiotic, preferably kanamycin, and diluting said first medium comprising the bacterial host with a second medium to an $OD_{600}$ of 0.1 to 0.4, preferably about 0.3, wherein said second medium is essentially free of an antibiotic, and further cultivating said bacterial host.

Furthermore, it is apparent for the skilled person, that the fermentation process of the invention is an aerobic process which requires adequate oxygen supply of the bacteria in the culture. The oxygen demand of the bacterial host is, inter alia, increasing with increasing cell density and increasing growth rate. Depending on the total volume and the oxygen demand of the bacterial host, oxygen can, for example, be supplied by stirring and/or by aeration with air. Alternatively, oxygen can also be supplied by aeration with pure oxygen or a mixture of pure oxygen with any other gas, preferably air, wherein pure oxygen refers to the technically pure gas as commonly available for technical purposes. A further possibility of supplying oxygen to the bacterial host is increasing the oxygen partial pressure in the medium by increasing the pressure in the fermenter.

In a preferred embodiment of the invention, said cultivating said bacterial host and/or said feeding of said batch culture and/or said inducing of said promoter with an inducer is performed under conditions, wherein said bacterial host is supplied with oxygen, preferably by aeration with air, most preferably by aeration with air in a constant flow, wherein preferably said oxygen is supplied throughout the entire process, most preferably throughout the lag-, growth- and production phase, and wherein further preferably the partial pressure of oxygen is monitored in the culture medium and wherein the bacterial host is alternatively or additionally supplied with oxygen by aeration with pure oxygen, preferably when the partial pressure of oxygen in the medium ($pO_2$) is below a certain threshold. In a specifically preferred embodiment said threshold of $pO_2$ is in the range of 0% to 60%, preferably 10% to 50%, more preferably 20% to 45% most preferably said threshold is about 40%.

Oxygen supply, preferably by aeration with air and/or pure oxygen to maintain the preferred $pO_2$ as described above, is routinely applied in the process of the invention, preferably for culture volumes of 2 l and more. Aeration with oxygen in the described manner is especially preferred in the scaled-up process, most preferably at 40 to 100 l and above.

Therefore, one embodiment of the invention is a process for expression of a recombinant capsid protein of a bacteriophage or a mutant or fragment thereof being capable of forming a VLP by self-assembly, said process comprising the steps of a) introducing an expression plasmid into a bacterial host, wherein said expression plasmid comprises an expression construct, wherein said expression construct comprises (i) a first nucleotide sequence encoding said recombinant capsid protein, or mutant or fragment thereof, and (ii) a promoter being inducible by lactose; b.) cultivating said bacterial host in a medium comprising a major carbon source; wherein said cultivating is performed in batch culture and under conditions under which said promoter is repressed by lacI, wherein said lacI is overexpressed by said bacterial host; c.) feeding said batch culture with said major carbon source; and d.) inducing said promoter with an inducer, wherein said feeding of said batch culture with said major carbon source is continued; wherein throughout steps b.) to d.) of said process oxygen is supplied to said bacterial host by a $pO_2$ in said medium of at least about 10% to 50%, preferably about 40%, and wherein further preferably said oxygen is supplied by aeration with air, pure oxygen, or a mixture of both, preferably by a mixture of air and pure oxygen.

EXAMPLES

Example 1

Cloning Strategy for the Expression Plasmid pTac-nSD-Qb-Mut (SEQ ID NO:1)

The coat protein-encoding gene (C) of E. coli RNA bacteriophage Qβ is amplified from plasmid pSDQb-rout (SEQ ID NO:33). The plasmid contains the sequence of gene C coding for the 133-aa Qβ coat protein (CP) and the 329-aa read through protein (A1). To prevent read-through, nucleotides 445-450 according to NCBI GenBank Acc. No. M99030 TGAACA (SEQ ID NO:31) are replaced by the sequence TAATGA (SEQ ID NO:32).

The coat protein-encoding gene C from plasmid pSDQb-mut is amplified by PCR. Oligonucleotide Qb-FOR3/2 (SEQ ID NO:34) with an internal EcoRI site and a synthetic Shine-Dalgarno (SD, SEQ ID No:4) sequence anneals to the 5' end of the Qβ CP gene. Oligonucleotide Qblang-REV2/2 (SEQ ID NO:35) contains an internal HindIII site and primes to the 3' end of the noncoding region of gene C. The 1054 bp amplified PCR fragment includes nucleotides 46-1062 of NCBI GenBank Acc. No. M99039 (except the nucleotide changes described above) and the synthetic SD sequence. The PCR fragment is digested with the restriction enzymes HindIII/EcoRI and the resulting 1036 bp fragment is inserted into the HindIII/EcoRI restriction sites of a modified pKK223-3 vector (Pharmacia, NCBI GenBank Acc. No.: M77749, SEQ ID NO:27). In this modified pKK223-3 vector the ampicillin resistance gene is replaced with the kanamycin resistance gene of vector pUC4K (Pharmacia, NCBI GenBank Acc. No.: X06404, SEQ ID NO:37).

Vector pTac-nSDQb-mut (SEQ ID NO:33) differs from vector pTacQb-mut in the Shine-Dalgarno sequence. This Shine-Dalgarno sequence (nSD, SEQ ID NO:3) is introduced by amplifying the Qβ coat protein-encoding gene C via PCR from plasmid pTacQb-mut. Oligonucleotide nSDQb-mutEcoRIfor (SEQ ID NO:36) with an internal EcoRI site and the corresponding synthetic Shine-Dalgarno (nSD) sequence anneals to the 5' end of the Qβ CP gene. Oligonucleotide Qblang-REV2/2 (SEQ ID NO:35) contains an internal HindIII site and primes to the 3' end of the noncoding region of gene C. The 1054 bp amplified PCR fragment includes nucleotides 46-1062 of NCBI GenBank Acc. No. M99039 (except the nucleotide changes described above) and the synthetic nSD sequence. The PCR fragment is digested with the restriction enzymes HindIII/EcoRI and the resulting 1036 bp fragment is inserted into the HindIII/EcoRI restriction sites of a modified pKK223-3 vector (Pharmacia, NCBI GenBank Acc. No.: M77749, SEQ ID NO:27). In this modified pKK223-3 vector the ampicillin resistance gene is replaced with the kanamycin resistance gene of vector pUC4K (Pharmacia, NCBI GenBank Acc. No.: X06404, SEQ ID NO:37).

Example 2

Cloning Strategy for the Expression Plasmid pTac-nSD-AP205 (SEQ ID NO:30)

The coat protein-encoding gene of *Acinetobacter* bacteriophage AP205 is amplified from plasmid pAP205-58. This plasmid contains the sequence of the coat protein gene (corresponding to nucleotides 1908-2303 of NCBI GenBank Acc. No. AF334111) coding for the 131-amino acid capsid protein of bacteriophage AP205.

The coat protein-encoding gene is amplified by PCR Oligonucleotide nSDAP238-EcoRIfor (SEQ ID NO:38) with an internal EcoRI site and a synthetic Shine-Dalgarno (nSD) sequence anneals to the 5' end of the coat protein gene. Oligonucleotide AP238HindIIIrev (SEQ ID NO:39) contains an internal HindIII site and primes to the 3' end of the coat protein gene. This oligonucleotid introduces a second stop codon behind the naturally occurring stop codon of the coat protein. Tie 438 bp amplified PCR fragment includes nucleotides 1908-2303 of NCBI GenBank Acc. No. AF334111 and the synthetic nSD sequence. The PCR fragment is digested with the restriction enzymes HindIII/EcoRI and the resulting 420 bp fragment is inserted into the HindIII/EcoRI restriction sites of a modified pKK223-3 vector (Pharmacia, NCBI GenBank Acc. No.: M77749, SEQ ID NO:27). In this modified pKK223-3 vector the ampicillin resistance gene is replaced with the kanamycin resistance gene of vector pUC4K (Pharmacia, NCBI GenBank Acc. No.: X06404, SEQ 11D NO:37).

Example 3

Expression of Qβ CP Under Control of the Tac Promoter and nSD

The *E. coli* strain RB791 was transformed with plasmids pTac-nSD-Qb-mut (SEQ ID NO:1). The clone was grown in shake flasks. Each flask contained 100 ml of R40 medium (main culture medium, Hypep 7455, glycerol, see Example 5) with kanamycin (25 μg/ml) and was inoculated with over night cultures at a start $OD_{600}$ of 0.3. The shake flasks were incubated for 4 h ($OD_{600}$ between 4 and 5) at 30° C. and an agitation of 220 rpm. The induction was carried out with 0.5% of lactose for 4 h. Protein production was determined by SDS-PAGE. The gel showed a strong protein band which was identified as Qβ CP.

Example 4

Expression of AP205 CP Under Control of the the Promoter and SD Vs. nSD 9 clones of pTac-nSDAP205 (SEQ ID NO:30) and 6 clones of pTac-SDAP205 were screened in shake flasks. pTac-SDAP205 (SEQ ID NO:40) is identical to pTac-nSDAP205 but comprises the Shine-Dalgarno sequence of SEQ ID NO:4 instead of that of SEQ ID NO:3. Each flask contained 50 ml of R40 medium (main culture medium, Hypep 7455, glycerol, see Example 5) with kanamycin (25 μg/ml) and was inoculated with over night cultures at a start $OD_{600}$ of 0.3 (for pTac-nSDAP205) or 0.4 (pTac-SDAP205). The shake flasks were incubated for 4 h at 30° C. and an agitation of 220 rpm. The induction was carried out with 0.5% of lactose. Protein production was determined by SDS-PAGE. For all tested clones expression of AP205 CP was significantly stronger from pTac-nSDAP205 than from pTac-SDAP205.

Example 5

Composition of Culture Media

Culture media were composed as described in Table 1.

TABLE 1

Composition of Culture media.

| | Concentrations in [g/L] | | | | |
|---|---|---|---|---|---|
| Component | Main Medium + Hypep R27 | Main Medium + Hypep + Glycerol R40 | Feed Medium + 50% Glycerol R41 | Induction Medium + 20% Glycerol + 20% Lactose R42 | Main Medium + Bacto YE + Glycerol R43 |
| $Na_2HPO_4 2H_2O$ | 2.5 | 2.5 | 2.5 | 2.5 | 2.5 |
| $KH_2PO_4$ | 3 | 3 | 3 | 3 | 3 |
| $K_2HPO_4$ | 5.2 | 5.2 | 5.2 | 5.2 | 5.2 |
| Citrate | 3.86 | 3.86 | 3.86 | 3.86 | 3.86 |
| $(NH_4)2SO_4$ | 4 | 4 | 4 | 4 | 4 |
| Vit B1 | 0.01 | 0.01 | 0.02 | 0.02 | 0.01 |
| $CaCl_2 2H_2O$ | 0.0147 | 0.0147 | 0.0147 | 0.0147 | 0.0147 |
| $MgSO_4 7H_2O$ | 0.5 | 0.5 | 9 | 9 | 0.5 |
| $FeCl_3 6H_2O$ | 0.054 | 0.054 | 0.054 | 0.054 | 0.054 |
| $CoCl_2 6H_2O$ | 0.0005 | 0.0005 | 0.0005 | 0.0005 | 0.0005 |
| $MnCl_2 4H_2O$ | 0.003 | 0.003 | 0.003 | 0.003 | 0.003 |
| $CuCl_2 2H_2O$ | 0.0003 | 0.0003 | 0.0003 | 0.0003 | 0.0003 |
| $H_3BO_3$ | 0.003 | 0.003 | 0.003 | 0.003 | 0.003 |
| $Na_2MoO_4 2H_2O$ | 0.0005 | 0.0005 | 0.0005 | 0.0005 | 0.0005 |
| $Zn(CH_3COO)_2 2H_2O$ | 0.0026 | 0.0026 | 0.0026 | 0.0026 | 0.0026 |
| Glucose | 5 | — | — | — | — |
| Glycerol | — | 5 | 500 | 200 | 5 |
| Lactose anhydrous | — | — | — | 200 | — |
| HyPep 7455 | 5 | 5 | — | — | — |
| Bacto Yeast Extract | — | — | — | — | 5 |

Example 6

Expression of Qβ CP in a Fed-Batch Process (2 L Scale)

The fermentation process was performed in a bioreactor (Applikon 5 L dished bottom) equipped with 2 disc stirrer (Ø6 cm), baffles (3×16 cm), pH-, pO2-, and temperature control, and fermenter software BioXpert Version 2.22

5 μL cryo culture of RB791 transformed with plasmids pTac-nSD-Qb-mut were inoculated in 100 mL Erlenmeyer flasks containing 50 mL medium R40 (25 μg/mL kanamycin) and cultivated for 14 h at 30° C. and 220 RPM over night. After 14 h an $OD_{600}$ value of 6.0 was reached. For batch fermentation, 2 L of medium (R40) were pumped into the bioreactor. In Table 2 the cultivation parameters are listed.

TABLE 2

Parameter set points for batch phase.

| Parameter | Set point | Unit |
| --- | --- | --- |
| Stirrer speed | 1000 | [rpm] |
| Air supply | 2.5 | [L/min] |
| O2-supply, maximal | 2 | [L/min] |
| Temperature | 30 | [° C.] |
| O2-saturation | >40 | [%] |
| pH | 6.8 | [—] |

The bioreactor was inoculated with 100 mL inoculum. Samples of 2 mL were taken, $OD_{600}$ determined and centrifuged at 14,000 RPM. Pellet and supernatant were separated and frozen for further analysis. The biomass concentration [g/L] was calculated using the following equation:

$$OD_{600} \times 0.45 \,[g \times L^{-1} \times OD_{600}^{-1}] = biomass\,[g/L].$$

The Qbeta content in percent of the total protein content was calculated as follows, assuming, that 50% of the E. coli biomass is protein:

$$Biomass\,[g \times L^{-1}]/2 = total\,protein\,[g \times L^{-1}]$$

$$Qbeta\,[g \times L^{-1}]/total\,protein\,[g \times L^{-1}] \times 100 = Qbeta/total\,protein\,[\%].$$

In the fed-batch mode, which followed the batch mode, a feeding phase was added. In the feeding phase substrate is supplied to the cells in the reactor according to a defined profile. The feed profile depends on the selected growth rate μ, the yield coefficient biomass to glycerol ($Y_{s/glycerol}$), the volume (Vf), and the concentration of substrate in the feed (cf). substrate concentration. The feed was calculated using the following equation:

Feed Equation $$mf = (\mu/Y_{X/S} + m) Vf \times Xf \times e^{\mu t}$$

$$pump = (mf/cf + b)/a$$

mf = mass flow [g/h]
μ = specific growth rate [1/h]
$Y_{X/Glycerol}$ = Yield biomass to glycerol [g/g]
m = maintenance energy [g·g$^{-1}$·h$^{-1}$]
Vf = Volume at feed start
Xf = Biomass at feed start
cf = Concentration of substrate in feed [g/mL]
a+b = offset slope of pump calibration equation For the determination of the calibration parameters a and b, a pump calibration was carried out. In addition, the feed tube with feed bottle was clamped into the feed pump and the pump was run with 7, 14 and 21% pump performance. The pumped feed volume per time was noted. In a resulting diagram of the relation of pump performance [%] to pumped feed solution [mL/h], the slope (a) and the Y-axis section (b) was determined. On the bioreactor the parameters in Table 3 were set for fed-batch cultivation.

TABLE 3

Parameters for fed-batch cultivation in bioreactor.

| Parameter | Set point | Unit |
| --- | --- | --- |
| Stirrer speed | 1000 | [rpm] |
| Air supply | 2.5 | [L/min] |
| O2-supply, maximal | 2 | [L/min] |
| Temperature | 30 | [° C.] |
| O2-saturation | >40 | [%] |
| pH | 6.8 | [—] |

After reaching a process time of approximately 7 h (end of batch) the feed pump was turned on automatically. After further 7 h cultivation, when the $OD_{600}$ reached 55-60, the feed medium (for biomass propagation) was exchanged with the induction medium R42 (for biomass propagation and induction). After 5 h feeding of R42 was stopped and the culture was harvested by centrifugation.

Analysis of Process Parameters:

The following process parameters were routinely analysed. The $pO_2$, pH, temperature and stirrer speed were measured online throughout the process time. The optical density was measured offline at 600 nm. The determination of the β-galactosidase activity was performed using a β-Gal Assay Kit (Invitrogen, cat. no. K1455-01). The activity was specified as units per mL $OD_{600} = 1.0$. It is defined as the quantity of Ortho-Nitrophenyl-β-D-Galactopyranosid (ONPG) in nmol, which is hydrolysed per minute and mL bacteria suspension ($OD_{600} = 1.0$). The accumulated product was analysed by SDS-PAGE, the total protein content (soluble and insoluble protein) was determined and using HPLC analysis, the soluble fraction was measured. Cell disruption of E. coli was performed in lysis buffer (50 mM glucose, 25 mM tris/HCl (pH 8), 15 mM EDTA (pH 8.0)) with and ultrasonic homogeniser (Bandlin Sonoplus, HD2070). 250 μL bacteria suspension with an $OD_{600}$ of 50 were centrifuged with 14000 RPM for 10 min. The pellet was resuspended in 250 μL lysis buffer (vortex) and placed at room temperature for 5 min. Afterwards, the cells were disrupted for 20 s with ultrasonic at 10% device performance (cells on ice) and then the cell suspension was centrifuged at 14000 RPM, 10 min. The supernatant (soluble protein) was then analysed by SDS-PAGE and HPLC.

Samples before induction and at end of production (after 5 h induction) were taken from the bioreactor for analysis of Qβ formation analyzed by SDS-PAGE standardized to OD 5.0. At the end of cultivation, 1.9 l of the culture was harvested. After centrifugation, the following cell pellets were obtained in three independent reactor runs: 1.) End $OD_{600}$ of 84: 194 g CWW; 2.) End $OD_{600}$ of 88: 200 g CWW; 3.) End $OD_{600}$ of 86: 201 g CWW.

The plasmid retention in run 1 and 2 was 100% at induction start and 100% at harvest. Based on comparison with a Qβ CP standard on SDS-PAGE the yield was roughly estimated to be about 5 g/l Qβ CP. HPLC analysis revealed a concentration of about 6 g/l Qβ VLP.

Example 7

Selection of Carbon Source and Bacterial Strain

Glucose and glycerol as carbon sources were compared. In order to test the growth behaviour of each of the strains DH20 and RB791 on these carbon sources, shake flask experiments wee conducted with medium containing glucose (R27) and medium containing glycerol (R40). Both media were supplemented with 25 µg/ml kanamycin. Each culture was started with an initial $OD_{600}$ of 0.3. Induction was performed by adding 0.5% lactose. The maximum specific growth rates ($\mu_{max}$) and the yield coefficients ($Y_{x/s}$) were determined and are listed in Table 4. RB791 grew faster on both, glucose and glycerol. In addition, the resulting yield coefficients were higher. Although glucose allowed higher maximum specific growth rates ($\mu_{max}$) the yield coefficients ($Y_{x/s}$) was higher for glycerol.

TABLE 4

Maximum specific growth rates and the yield coefficients of the cultivation experiments with RB791 and DH20 on glucose and glycerol.

| Strain | Carbon source | Value after 4.5 h Culture Time | | Max. spec. growth rate ($\mu_{max}$) [$h^{-1}$] | Yield coefficient ($Y_{x/s}$) biomass from substrate [g/g] |
|---|---|---|---|---|---|
| | | $OD_{600}$ | Acetate [$gl^{-1}$] | | |
| RB791 | glucose | 6.24 | 0.44 | 0.71 | 0.72 |
| | glycerol | 4.04 | 0.21 | 0.62 | 0.86 |
| DH20 | glucose | 2.52 | 0.42 | 0.51 | 0.71 |
| | glycerol | 2.82 | 0.25 | 0.50 | 0.81 |

Example 8

Determination of Optimal Temperature

The influence of temperature on product formation was investigated. Two shake flask cultures were inoculated and incubated at 30° C. and 220 rpm. After an $OD_{600}$ of 5 was reached, the cultures were induced with lactose. Subsequently, one culture was continued to be incubated at 37° C. and the other culture at 23° C. Results of the SDS-PAGE revealed that expression levels at 4 and 5 h after induction are higher in the culture induced at 37° C. Induction of the cultures for 19 h showed a higher Qβ level in the cultures induced at 23° C.

Example 9

Induction by Co-Feed of Lactose and Glycerol

A feed solution of 20% glycerol and 20% lactose was composed (R42) and applied to fermentation as described in Example 6 at induction start. FIG. 1 provides an overview over relevant process parameters throughout the entire process time. Expression was induced at 13.5 h at an $OD_{600}$ of about 55. Upon induction, the feed pump rate was set to constant. Glycerol did not accumulate with feeding. Lactose accumulated to 4 g/l and then it started to diminish. The β-galactosidase activity rose to 10 U/ml and decreased thereafter. Compared with the previous fermentation runs a.) lactose applied as a single lactose pulse at induction start, no feeding; b.) continuous lactose feed without glycerol, the activity was with 7 U/ml higher and the maximum activity was already reached after 2 h as compared to 4 h in runs a.) and b.).

Example 10

Plasmid Retention

The effect of the following operating conditions on the plasmid retention was tested in the process described in Example 6: 1.) Preculture starting volume, 2.) Kanamycin in the preculture, 3.) Growth and/or induction at 37° C. vs. 30° C. The results are summarised in Table 5. Precultures were started with volumes of 5 µl out of the cell bank vial. Inoculation of a small volume allowed growth of a preculture over-night. The preculture for QT0103_F8 contained 25 mg/l kanamycin, whereas the preculture for QT0103_F7 did not contain any kanamycin. Both fermentations were operated at 30° C. and induced for 5 h. Judging from the plasmid retentions before and after 5 h induction, supplementing the preculture with kanamycin has a positive effect on plasmid retention. Plasmid retention remained at 98% before and after 5 h induction. In contrast, plasmid retentions reached only values of 80% when kanamycin was omitted from the preculture. For a subsequent run, QT0203_F7, the preculture was also started with 5 µl and grown in kanamycin containing medium. The resulting fermentation in the bioreactor was operated at 37° C. from the beginning. Operation at 37° C. had a detrimental effect on the plasmid stability. While the plasmid retention was at 99% before induction, it dropped to 0% after 5 h induction. In order to test whether a shorter preculture and thus, less generations, would improve the plasmid retention after 5 h induction, a set of precultures were started with 300 µl volume from a thawed cell bank vial and grown in kanamycin free medium. Two fermenters were operated at 30° C. for the whole run. An additional two fermenters were operated first at 30° C. for cell growth and than switched to 37° C. for the production phase. The resulting plasmid stabilities were all at 100% before and 5 h after induction.

TABLE 5

Summary of plasmid retention before and 5 h after induction obtained under different operating conditions in terms of generations in the preculture, with and without kanamycin in the preculture, and growth and/or induction at 37° C.

| Bioreactor run | Preculture Starting Culture Volume [µl] | Kanamycin in preculture | Plasmid retention before induc. [%] | Plasmid retention after 5 h induc. [%] | Remarks |
|---|---|---|---|---|---|
| QT0103_F8 | 5 | 25 mg/L | 98 | 98 | whole process at 30° C. |
| QT0103_F7 | 5 | no | 80 | 80 | whole process at 30° C. |
| QT0203_F7 | 5 | 25 mg/L | 99 | 0 | Bioreactor run at 37° C. |
| QT0603_F7 | 300 | no | 100 | 100 | whole process at 30° C. |
| QT0703_F8 | 300 | no | 100 | 100 | Induction at 37° C., rest of the process at 30° C. |

TABLE 5-continued

Summary of plasmid retention before and 5 h after induction obtained under different operating conditions in terms of generations in the preculture, with and without kanamycin in the preculture, and growth and/or induction at 37° C.

| Bioreactor run | Preculture Starting Culture Volume [µl] | Kanamycin in preculture | Plasmid retention before induc. [%] | Plasmid retention after 5 h induc. [%] | Remarks |
|---|---|---|---|---|---|
| QT0803_F9 | 300 | no | 100 | 100 | whole process at 30° C. |
| QT0903_F10 | 300 | no | 100 | 100 | Induction at 37° C., rest of the process at 30° C. |

Example 11

Variation in Time Point of Induction

In a process essentially as described in Example 6 the exponential feed profile was programmed to start 7 h after the inoculation of the bioreactor. Under standard conditions, the scheduled time for induction was at 14 h process time. In order to test the effect of variations in the time point of induction on the final cell densities, one culture was induced at 13.5 h (resulting in 6.5 h of exponential feed) and another culture at 14.5 h (resulting in 7.5 h of exponential feed). One culture induced at the regular 14 h time point served as a control (7 h of exponential feed). Results are summarised in Table 6. Cell density increased with increasing length of feeding, Judged from a linear regression analysis of the available data points for final CWW, a linear relationship appears to exist ($r^2=0.92$).

TABLE 6

Variations in time point of induction: effect on final cell density in terms of $OD_{600}$ and CWW.

| Reactor | Process Time Point of Induction | Duration of Exp. Feed Phase [h] | Final $OD_{600}$ | Final CWW [g/L] |
|---|---|---|---|---|
| F2 | 13 h 32 min | 6.5 | 83.4 | 116.5 |
| F1 | 14 h 02 min | 7.0 | 82.4 | 122.5 |
| F3 | 14 h 29 min | 7.5 | 100.4 | 141.1 |

Example 12

Variation in Time Point of Harvest

Harvest of the culture in a process essentially as described in Example 6 is performed manually. Under standard conditions, the scheduled time for harvest was at 19 h process time. The operation "Harvest" involves the manual ending of the bioreactor operations. In order to test the effect of variations in the time point of harvest on the final cell densities, one culture was harvested at 18.8 h (resulting in 4.8 h of induction) and another culture at 19.5 h (resulting in 5.5 h of induction). One culture harvested at the regular 19 h time point served as a control (5 h of induction). Results are summarized in Table 7. Cell density increased with increasing length of induction because the cells are still growing while induced.

TABLE 7

Variation in time point of harvest: effect on final cell density in terms of OD600 and CWW.

| Reactor | Process Time Point of Harvest | Length of Induction [h] | Final $OD_{600}$ | Final CWW [g/L] |
|---|---|---|---|---|
| F5 | 18 h 50 min | 4.8 | 91.4 | 122.4 |
| F4 | 19 h 00 min | 5.0 | 92.2 | 127.5 |
| F6 | 19 h 30 min | 5.5 | 96.0 | 132.4 |

Example 13

Effect of Temperature

The effect of fermentation temperature in a process essentially as described in Example 6 was investigated by running 6 fermentations at 5 different temperature setpoints. Results are summarized in Table 8. Final cell densities were sensitive to the fermentation temperature with an optimum at a temperature of 30° C.

TABLE 8

Summarized results of different temperature setpoints on final cell density in terms of OD600 and CWW.

| Reactor | Temperature [° C.] | Final $OD_{600}$ | Final CWW [g/L] |
|---|---|---|---|
| F5 | 25.0 | 37.8 | 62 |
| F4 | 27.5 | 80.0 | 117 |
| F3 | 30.0 | 92.8 | 123 |
| F4 | 30.0 | 92.4 | 125 |
| F5 | 32.5 | 85.0 | 111 |
| F6 | 35.0 | 79.6 | 107 |

Example 14

Scaled-Up Fermentation (50 l)

The process described in Example 6 was scaled up to a volume of 50 i order to evaluate scale-up capability from the 2 L working volume bioreactor system to a larger volume. Key process parameters for the scaled-up process are summarized in Table 9.

TABLE 9

Process parameters of in 50 L bioreactor.

| Culture Step | Description | Time [h] | OD$_{600}$ |
|---|---|---|---|
| Preculture 1 | 300 μl from cell bank vial are transferred into 100 ml preculture medium contained in 500 mL shake flask and cultured for 16 h | −11* | 5.0 |
| Preculture 2 | Calculate the required volume for transfer in order to start with initial OD$_{600}$ of 0.3 in 750 ml. Tranfer calculated volume (e.g. 50 ml) into 750 ml preculture medium contained in 5000 mL shake flask | −5* | 4.0 |
| Inoculation of Bioreactor | Pooled calculated volume (e.g. 1.4 L) is transferred into the 50 L Bioreactor. Initial volume: = 40 L | 0 | |
| Induction Start | The exponential feeding profile is switched to constant and feed is switched to induction feed | 14 | 46 |
| End of Culture | Culture is completed after 5 h of induction | 19 | 128 |

*Relative to the time of bioreactor inoculation.

It was necessary to have two preculture expansion steps. In the first step, the cells were expanded as established for the 2 L process (Example 6). After this step, cells were split into two 5000 ml shake flask cultures, containing 750 ml medium each. Further expansion was performed for 5 h. The cultures in the 50 L bioreactors were performed with the same time profile as in the 2 L system (Example 6). OD$_{600}$ at induction start was 46, the final OD$_{600}$ was 128. Plasmid retention was 100% before induction and 98% at the end of culture. The concentration of Qβ CP protein in the medium at the end of culture was roughly estimated 8 g/l using SDS-PAGE. The total amount of Qβ was estimated about 300 g for this reactor run.

Example 15

Effect of Extended Exponential Feed

The exponential feeding phase for fermentations performed according to Examples 6 or 14 was 7 h. After this time the cells reached a density for induction, which increased during induction to the targeted maximum OD$_{600}$ of around 100 to 130 as final cell density. Final OD$_{600}$, final CWW, final CDW, plasmid retention at induction start and harvest and Qβ concentration at the end of culture are determined for reactor runs performed as described in Examples 6 and 14, as in Example 14, wherein the exponential feeding phase is extended to a duration up to 11 h, preferably to 10 h.

Example 16

Effect of Increased Feeding During Production

Example 9 demonstrates that the glycerol does not accumulate during production phase, indicating that production might be limited by the feeding rate of induction medium. Effect of extended feeding rate of induction medium on final OD$_{600}$, final CWW, final CDW, plasmid retention at induction start and harvest and Qβ concentration at the end of culture is determined in reactor runs as described in Example 6 and 14, preferably as in Example 14, wherein the feeding rate during production is increased. Alternatively or additionally, the ratio between lactose and glycerol in the feed medium shifted towards a higher glycerol and a lower lactose concentration.

Example 17

HPLC Analysis of Qβ CP

Qβ CP was measured with an HPLC system as follows: A sample containing Qβ CP was diluted appropriately in 1× reaction buffer (50 mM tris(hydroxymethyl)aminomethane buffer pH 8.0) containing 10 mM 1,4-Dithio-DL-threitol and incubated for 15 min at 50° C. in a thermomixer. After incubation the sample was centrifuged and the supernatant was stored at 2° C. to 10° C. until HPLC analysis. 10 to 100 μl of the sample were injected.

Qβ was quantified with a regression curve of known Qβ standards regressed to the HPLC peak area detected at 215 nm after elution from a C$_4$ reversed phase column, 300 Å, 5 μm, 4.6×150 mm, Vydac Inc., Hesperia, USA (Cat. No. 214TP5415) thermally equilibrated at 50° C. The flow rate through the system was 1 ml/min consisting of mobile phase A (0.12% trifluoroacetic acid in water) and mobile phase B (0.12% trifluoroacetic acid in acetonitrile) with the following gradient of phase B: 0 to 2 min constant at 40%, 2 to 8 min linear increase to 50%, 8 to 10 min constant at 50%, 10 to 10.1 min linear decrease to 40%, and 10.1 to 12 min constant at 40%.

Example 18

Determination of Qβ VLP by Analytical Size Exclusion Chromatography

Analysis of Qβ particles by analytical size exclusion chromatography was performed using a TskgelG5000 PW$_{XL}$-column (10 μm, 7.8×300 mm, TosoH Biosep; Cat.-No. 08023) equilibrated in phosphate buffered saline (20 mM Na$_2$HPO$_4$/NaH$_2$PO$_4$, 150 mM NaCl pH 7.2). Elution was performed by an isocratic gradient for 20 min at 0.8 ml/min in phosphate buffered saline. The Qbeta concentration was determined from a regression curve of known Qβ standards regressed to the HPLC peak area detected at 260 nm.

Example 19

Effect of Extended Exponential Feed

The exponential feeding phase for fermentations performed according to Examples 6 or 14 was 7 h. After this time the cells reached a density for induction, which increased during induction to the targeted maximum OD$_{600}$ of around 100 to 130 as final cell density. Final OD$_{600}$, final CWW, plasmid retention before induction and at harvest and Qβ concentration at the end of culture were determined for reactor runs performed as described in Examples 6 and 14, preferably as in Example 14, wherein the exponential feeding phase was extended to a duration up to 12 h. In addition, the concentration of glycerol and lactose in the induction feed were changed to 300 g/L and 100 g/L respectively. The results are summarized in Table 10.

TABLE 10

OD$_{600}$ and CWW at the end of cultivations, Plasmid Retention before induction and at the end of cultivation as well as the peak oxygen mass flow. The cultivation were conducted with different duration of exponential feeding.

| Duration Exponential Feeding [h] | OD$_{600}$ [—] | CWW [g/L] | Plasmid Retention [%] before induction | Plasmid Retention [%] end of cultivation | Peak Oxygen Mass Flow [vvm] |
|---|---|---|---|---|---|
| 7  | 86  | 122 | 100 | 99  | 0.2  |
| 8  | 112 | 184 | 99  | 98  | 0.4  |
| 9  | 136 | 217 | 100 | 98  | 0.8  |
| 10 | 164 | 228 | 99  | 98  | 1.5  |
| 11 | 200 | 262 | 100 | 97  | >4.5 |
| 12 | 90  | 186 | 99  | 100 | >4.5 |

According to LDS-PAGE analysis, the specific Qbeta concentration of all cultivations except for the cultivation with 12 h exponential feeding was the same. An optimum regarding absolute Qbeta yield and oxygen consumption was found for 9.5 h exponential feeding. Therefore, the process is preferably run with 9.5 h exponential feeding phase.

Example 20

Scaled Up Fermentation (50 l)

The process described in Example 6 and with 9.5 h exponential feeding phase with 300 g/L, glycerol and 100 g/L lactose as described in Example 19 was scaled up to a volume of 50 L in order to evaluate scale-up capability from the 2 L working volume bioreactor system to a larger volume. Key process parameters for the scaled up process are summarized in Table 11.

TABLE 11

Process parameters on the 50 L scale

| Culture Step | Description | Time [h] |
|---|---|---|
| Preculture | 200 μl from cell bank vial were transferred into 800 ml preculture medium contained in 3000 mL shake flask and cultured for 18 h (2 flasks) | −18* |
| Inoculation of Bioreactor | Pooled total volume (approx. 1.6 L) was transferred into the 50 L Bioreactor. Initial volume: = 35 L | 0 |
| Induction Start | The exponential feeding profile was switched to constant and feed was switched to induction feed | 16.5 |
| End of Culture | Culture was completed after 5 h of induction | 21.5 |

*Relative to the time of bioreactor inoculation.

It was necessary to change the preculture procedure in order to inoculate the larger reactor with approximately the same cell density. The cultures in the 50 L bioreactors were performed with the time profile optimised for the 2 L scale as described in Example 19. The final cell wet weight for six cultivations was 188 g/L±9. Plasmid retention was 97.3%±1.4 at the end of culture. The concentration of Qβ CP protein in the medium at the end of culture was determined by C$_4$ reversed phase HPLC (Example 17) to 10.8 g/L±0.3. The total amount of Qβ CP was 540 g for one 50 L run. The crude extract of approximately two times concentrated biomass was analysed for Qβ CP and Qβ VLP (Example 18). The concentration of Qβ CP was 19.1 g/L±0.4 (C$_4$ reversed phase HPLC), the concentration of Qβ VLP was 18.8 g/L±1.1. Therefore, the VLP-yield of the fermentation process is estimated to approximately 9-11 g/l fermentation broth at the time of harvest.

The invention claimed is:

1. A process for producing a recombinant capsid protein of a RNA bacteriophage being capable of forming a virus-like particle (VLP) by self-assembly, wherein said RNA bacteriophage is RNA bacteriophage Qβ, and wherein said recombinant capsid protein has the amino acid sequence of SEQ ID NO:5, said process comprising the steps of:
   a) introducing an expression plasmid consisting of SEQ ID NO: 1 into a bacterial host, wherein said expression plasmid comprises (i) a first nucleotide sequence of SEQ ID NO:6 encoding said recombinant capsid protein, and (ii) a promoter inducible by lactose;
   b) initiating a growth phase by cultivating said bacterial host in a medium comprising a major carbon source; wherein said cultivating initiates a batch phase during said growth phase, wherein said cultivating is performed in batch culture and under conditions under which said promoter is repressed by lacI, wherein said lacI is overexpressed by said bacterial host, and wherein no feeding of said batch culture is performed during said cultivating;
   c) ending said batch phase and initiating a feed phase during said growth phase by feeding said batch culture with said major carbon source; wherein said feeding of said batch culture is performed with a flow rate, wherein said flow rate increases with an exponential coefficient μ, and
   d) ending said growth phase and initiating a production phase by inducing said promoter with an inducer that is lactose, wherein said lactose and said major carbon source are co-fed to said batch culture in a ratio of 2:1 to 1:4 (w/w) and wherein said cultivating and feeding of said batch culture and said inducing of said promoter is performed at a temperature between 23° C. and 35° C.; and
   wherein said steps (b), (c) and (d) are performed without removal of medium, except for analytical purposes, and said steps result in an increase of the density of said bacterial host in said medium; thereby producing said recombinant capsid protein of the RNA bacteriophage being capable of forming said VLP.

2. The process of claim 1, wherein said expression construct comprises a first stop codon and a second stop codon, wherein said first stop codon is located directly 3' of said first nucleotide sequence and wherein said second stop codon is located directly 3' of said first stop codon, and wherein at least one of said first or second stop codon is TAA.

3. The process of claim 1, wherein said expression construct comprises a first nucleotide sequence and a second nucleotide sequence, wherein said first nucleotide sequence is encoding Qβ coat protein (CP), and wherein said second nucleotide sequence is encoding Qβ A1 protein and wherein said first and said second nucleotide sequence are separated by exactly one sequence stretch comprising at least one TAA stop codon.

4. The process of claim 1, wherein said major carbon source is glycerol.

5. The process of claim 1, wherein said exponential coefficient μ is below $\mu_{max}$.

6. The process of claim 1, wherein said inducing of said promoter is performed by co-feeding said batch culture with said inducer and said major carbon source at a constant flow rate.

7. The process of claim 6, wherein said inducer is lactose and wherein said lactose and said major carbon source are co-fed to said batch culture in a ratio of about 2:1 to 1:4 (w/w).

8. The process of claim 1, wherein said inducing of said promoter is performed by co-feeding said batch culture with said inducer and said major carbon source at an increasing flow rate.

9. The process of claim 8, wherein said inducer is lactose and wherein said lactose and said major carbon source are co-fed to said batch culture in a ratio of about 2:1 to 1:4 (w/w).

10. The process of claim 1, wherein said inducer is IPTG and wherein the concentration of said IPTG in said medium is 0.001 to 5 mM.

11. The process of claim 1, wherein said lacI is overexpressed by said bacterial host, wherein said overexpression is caused by $lacI^q$ or lacQ1.

12. The process of claim 1, wherein said inducer is lactose and wherein said bacterial host comprises β-galactosidase activity.

13. The process of claim 1, wherein said cultivating and said feeding of said batch culture and said inducing of said promoter is performed at a temperature which is below the optimal growth temperature of said bacterial host.

14. The process of claim 1, wherein throughout steps b.) to d.) of said process oxygen is supplied to said bacterial host, wherein said oxygen supply is effected such that the partial pressure of oxygen in the medium ($pO_2$) is at least about 40%.

15. The process of claim 1, wherein said lactose and said major carbon source are co-fed to said batch culture in a ratio of 1:1 to 1:3 (w/w).

16. The process of claim 1, wherein said lactose and said major carbon source are co-fed to said batch culture in a ratio of 1:3 (w/w).

17. The process of claim 1, wherein said promoter is selected from the group consisting of the
   a.) tac promoter;
   b.) trc promoter;
   c.) tic promoter;
   d.) lac promoter;
   e.) lacUV5 promoter;
   f.) $P_{syn}$ promoter;
   g.) $lpp^a$ promoter;
   h.) lpp-lac promoter;
   i.) T7-lac promoter;
   j.) T3-lac promoter;
   k.) T5-lac promoter; and
   l.) a promoter having at least 50% sequence homology to SEQ ID NO:2.

18. The process of claim 1, wherein said promoter comprises the nucleotide sequence of SEQ ID NO:2.

19. The process of claim 1, wherein:
a.) said major carbon source is glycerol;
b.) said bacterial host is *E. coli* RB791; and
c.) said cultivating and feeding of said batch culture and said inducing of said promoter is performed at a temperature of about 30° C.

20. The process of claim 1, wherein said lacI is overexpressed by said bacterial host, wherein said overexpression is caused by lacI$^q$.

* * * * *

SEQUENCE LISTING

<160> NUMBER OF SEQ ID NOS: 40

<210> SEQ ID NO 1
<211> LENGTH: 5579
<212> TYPE: DNA
<213> ORGANISM: artificial sequence
<220> FEATURE:
<223> OTHER INFORMATION: plasmid - chemically synthesized

<400> SEQUENCE: 1

```
ggctgtgcag gtcgtaaatc actgcataat tcgtgtcgct caaggcgcac tcccgttctg      60
gataatgttt tttgcgccga catcataacg gttctggcaa atattctgaa atgagctgtt     120
gacaattaat catcggctcg tataatgtgt ggaattgtga gcggataaca atttcacaca     180
ggaaacagaa ttctaaggag gaaaaaaaaa tggcaaaatt agagactgtt actttaggta     240
acatcgggaa agatggaaaa caaactctgg tcctcaatcc gcgtgtggta aatcccacta     300
acggcgttgc ctcgctttca caagcgggtg cagttcctgc gctggagaag cgtgttaccg     360
tttcggtatc tcagccttct cgcaatcgta agaactacaa ggtccaggtt aagatccaga     420
acccgaccgc ttgcactgca aacggttctt gtgacccatc cgttactcgc caggcatatg     480
ctgacgtgac cttttcgttc acgcagtata gtaccgatga ggaacgagct tttgttcgta     540
cagagcttgc tgctctgctc gctagtcctc tgctgatcga tgctattgat cagctgaacc     600
cagcgtatta atgactgctc attgccggtg gtggctcagg gtcaaaaccc gatccggtta     660
```

```
ttccggatcc accgattgat ccgccgccag ggacaggtaa gtatacctgt cccttcgcaa      720
tttggtccct agaggaggtt tacgagcctc tactaagaa ccgaccgtgg cctatctata       780
atgctgttga actccagcct cgcgaatttg atgttgccct caaagatctt ttgggcaata      840
caaagtggcg tgattgggat tctcggctta gttataccac gttccgcggt tgccgtggca      900
atggttatat tgaccttgat gcgacttatc ttgctactga tcaggctatg cgtgatcaga      960
agtatgatat tcgcgagggc aagaaacctg gtgctttcgg taacattgag cgattcattt     1020
atcttaagtc gataaatgct tattgctctc ttagcgatat tgcggcctat cacgccgatg     1080
gcgtgatagt tggcttttgg cgcgatccat ccagtggtgg tgccataccg tttgacttca     1140
ctaagtttga taagactaaa tgtcctattc aagccgtgat agtcgttcct cgtgcttagt     1200
aactaaggat gaaatgcatg tctaagcttg gctgttttgg cggatgagag aagattttca     1260
gcctgataca gattaaatca gaacgcagaa gcggtctgat aaaacagaat ttgcctggcg     1320
gcagtagcgc ggtggtccca cctgacccca tgccgaactc agaagtgaaa cgccgtagcg     1380
ccgatggtag tgtggggtct ccccatgcga gagtagggaa ctgccaggca tcaaataaaa     1440
cgaaaggctc agtcgaaaga ctgggccttt cgttttatct gttgtttgtc ggtgaacgct     1500
ctcctgagta ggacaaatcc gccggagcg gatttgaacg ttgcgaagca acggcccgga     1560
gggtggcggg caggacgccc gccataaact gccaggcatc aaattaagca gaaggccatc     1620
ctgacggatg ccttttttgc gtttctacaa actctttttgt ttattttttct agagccacgt    1680 tgtgtctcaa aatctctgat gttacattgc acaagataaa aatatatcat catgaacaat     1740
aaaactgtct gcttacataa acagtaatac aaggagtgtt atgagccata ttcaacggga     1800
aacgtcttgc tcgaggccgc gattaaattc caacatggat gctgatttat atgggtataa     1860
atgggctcgc gataatgtcg ggcaatcagg tgcgacaatc tatcgattgt atgggaagcc     1920
cgatgcgcca gagttgtttc tgaaacatgg caaaggtagc gttgccaatg atgttacaga     1980
tgagatggtc agactaaact ggctgacgga atttatgcct cttccgacca tcaagcattt     2040
tatccgtact cctgatgatg catggttact caccactgcg atccccggga aaacagcatt     2100
ccaggtatta gaagaatatc ctgattcagg tgaaaatatt gttgatgcgc tggcagtgtt     2160
cctgcgccgg ttgcattcga ttcctgtttg taattgtcct tttaacagcg atcgcgtatt     2220
tcgtctcgct caggcgcaat cacgaatgaa taacggtttg gttgatgcga gtgattttga     2280
tgacgagcgt aatggctggc ctgttgaaca gtctggaaa gaaatgcata agcttttgcc     2340
attctcaccg gattcagtcg tcactcatgg tgatttctca cttgataacc ttattttga      2400 cgagggaaa ttaataggtt gtattgatgt tggacgagtc ggaatcgcag accgatacca     2460
ggatcttgcc atcctatgga actgcctcgg tgagttttct ccttcattac agaaacggct     2520
ttttcaaaaa tatggtattg ataatcctga tatgaataaa ttgcagtttc atttgatgct     2580
cgatgagttt ttctaaacgc gtgaccaagt ttactcatat gtactttaga ttgatttaaa     2640
acttcatttt taatttaaaa ggatctaggt gaagatcctt tttgataatc tcatgaccaa     2700
aatcccttaa cgtgagtttt cgttccactg agcgtcagac cccgtagaaa agatcaaagg     2760
atcttcttga tccttttttt ttctgcgcgt aatctgctgc ttgcaaacaa aaaaaccacc     2820
gctaccagcg gtggtttgtt tgccggatca agagctacca actctttttc cgaaggtaac     2880
tggcttcagc agagcgcaga taccaaatac tgtccttcta gtgtagccgt agttaggcca     2940
ccacttcaag aactctgtag caccgcctac atacctcgct ctgctaatcc tgttaccagt     3000
```

```
ggctgctgcc agtggcgata agtcgtgtct taccgggttg gactcaagac gatagttacc    3060
ggataaggcg cagcggtcgg gctgaacggg gggttcgtgc acacagccca gcttggagcg    3120
aacgacctac accgaactga gatacctaca gcgtgagcta tgagaaagcg ccacgcttcc    3180
cgaagggaga aaggcggaca ggtatccggt aagcggcagg gtcggaacag gagagcgcac    3240
gagggagctc caggggggaa acgcctggta tctttatagt cctgtcgggt ttcgccacct    3300
ctgacttgag cgtcgatttt tgtgatgctc gtcaggggg cggagcctat ggaaaaacgc     3360
cagcaacgcg gcctttttac ggttcctggc cttttgctgg ccttttgctc acatgttctt    3420
tcctgcgtta tcccctgatt ctgtggataa ccgtattacc gcctttgagt gagctgatac    3480
cgctcgccgc agccgaacga ccgagcgcag cgagtcagtg agcgaggaag cggaagagcg    3540
cctgatgcgg tattttctcc ttacgcatct gtgcggtatt tcacaccgca tatggtgcac    3600
tctcagtaca atctgctctg atgccgcata gttaagccag tatacactcc gctatcgcta    3660
cgtgactggg tcatggctgc gccccgacac ccgccaacac ccgctgacgc gccctgacgg    3720
gcttgtctgc tcccggcatc cgcttacaga caagctgtga ccgtctccgg gagctgcatg    3780
tgtcagaggt tttcaccgtc atcaccgaaa cgcgcgaggc agctgcggta aagctcatca    3840
gcgtggtcgt gaagcgattc acagatgtct gcctgttcat ccgcgtccag ctcgttgagt    3900
ttctccagaa gcgttaatgt ctggcttctg ataaagcggg ccatgttaag gcggtttttt    3960
tcctgtttgg tcactgatgc ctccgtgtaa gggggatttc tgttcatggg ggtaatgata    4020
ccgatgaaac gagagaggat gctcacgata cgggttactg atgatgaaca tgcccggtta    4080
ctggaacgtt gtgagggtaa acaactggcg gtatggatgc ggcgggacca gagaaaaatc    4140
actcagggtc aatgccagcg cttcgttaat acagatgtag gtgttccaca gggtagccag    4200
cagcatcctg cgatgcagat ccggaacata atggtgcagg cgctgacttc cgcgttttcc    4260
agactttacg aaacacggaa accgaagacc attcatgttg ttgctcaggt cgcagacgtt    4320
ttgcagcagc agtcgcttca cgttcgctcg cgtatcggtg attcattctg ctaaccagta    4380
aggcaacccc gccagcctag ccgggtcctc aacgacagga gcacgatcat gcgcacccgt    4440
ggccaggacc aacgctgccc gagatgcgcc gcgtgcggc tgctggagat ggcggacgcg     4500
atggatatgt tctgccaagg gttggtttgc gcattcacag ttctccgcaa gaattgattg    4560
gctccaattc ttggagtggt gaatccgtta gcgaggtgcc gccggcttcc attcaggtcg    4620
aggtggcccg gctccatgca ccgcgacgca acgcggggag gcagacaagg tatagggcgg    4680
cgcctacaat ccatgccaac ccgttccatg tgctcgccga ggcggcataa atcgccgtga    4740
cgatcagcgg tccaatgatc gaagttaggc tggtaagagc cgcgagcgat ccttgaagct    4800
gtccctgatg tcgtcatct acctgcctgg acagcatggc ctgcaacgcg gcatcccga     4860
tgccgccgga agcgagaaga atcataatgg ggaaggccat ccagcctcgc gtcgcgaacg    4920
ccagcaagac gtagcccagc gcgtcggccg ccatgccggc gataatggcc tgcttctcgc    4980
cgaaacgttt ggtggcggga ccagtgacga aggcttgagc gagggcgtgc aagattccga    5040
ataccgcaag cgacaggccg atcatcgtcg cgctccagcg aaagcggtcc tcgccgaaaa    5100
tgacccagag cgctgccggc acctgtccta cgagttgcat gataaagaag acagtcataa    5160
gtgcggcgac gatagtcatg ccccgcgccc accggaagga gctgactggg ttgaaggctc    5220
tcaagggcat cggtcgacgc tctcccttat gcgactcctg cattaggaag cagcccagta    5280
gtaggttgag gccgttgagc accgccgccg caaggaatgg tgcatgcaag agatggcgc    5340
ccaacagtcc cccggccacg gggcctgcca ccatacccac gccgaaacaa gcgctcatga    5400
```

-continued

```
gcccgaagtg gcgagcccga tcttccccat cggtgatgtc ggcgatatag gcgccagcaa    5460
ccgcacctgt ggcgccggtg atgccggcca cgatgcgtcc ggcgtagagg atccgggctt    5520
atcgactgca cggtgcacca atgcttctgg cgtcaggcag ccatcggaag ctgtggtat     5579
```

```
<210> SEQ ID NO 2
<211> LENGTH: 245
<212> TYPE: DNA
<213> ORGANISM: artificial sequence
<220> FEATURE:
<223> OTHER INFORMATION: promoter sequence - chemically synthesized

<400> SEQUENCE: 2
cgactgcacg gtgcaccaat gcttctggcg tcaggcagcc atcggaagct gtggtatggc     60
tgtgcaggtc gtaaatcact gcataattcg tgtcgctcaa ggcgcactcc cgttctggat    120
aatgtttttt gcgccgacat cataacggtt ctggcaaata ttctgaaatg agctgttgac    180
aattaatcat cggctcgtat aatgtgtgga attgtgagcg ataacaatt tcacacagga    240 aacag                                                               245
```

```
<210> SEQ ID NO 3
<211> LENGTH: 19
<212> TYPE: DNA
<213> ORGANISM: artificial sequence
<220> FEATURE:
<223> OTHER INFORMATION: Shine-Dalgarno Sequence - chemically
      synthesized

<400> SEQUENCE: 3
taaggaggaa aaaaaaatg                                                  19
```

```
<210> SEQ ID NO 4
<211> LENGTH: 18
<212> TYPE: DNA
<213> ORGANISM: artificial sequence
<220> FEATURE:
<223> OTHER INFORMATION: Shine-Dalgarno Sequence - chemically
      synthesized

<400> SEQUENCE: 4
aggaggtaaa aaacgatg                                                   18
```

```
<210> SEQ ID NO 5
<211> LENGTH: 133
<212> TYPE: PRT
<213> ORGANISM: Bacteriophage Q-beta

<400> SEQUENCE: 5
```

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
                20                  25                  30

Val Ala Ser Leu Ser Gln Ala Gly Ala Val Pro Ala Leu Glu Lys Arg
            35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 6
<211> LENGTH: 1017
<212> TYPE: DNA
<213> ORGANISM: artificial sequence
<220> FEATURE:
<223> OTHER INFORMATION: Expression construct - chemically synthesized

<400> SEQUENCE: 6

```
atggcaaaat tagagactgt tactttaggt aacatcggga agatggaaaa caaaactctg      60
gtcctcaatc cgcgtggggt aaatcccact aacggcgttg cctcgctttc acaagcgggt     120
gcagttcctg cgctggagaa gcgtgttacc gtttcggtat ctcagccttc tcgcaatcgt     180
aagaactaca aggtccaggt taagatccag aacccgaccg cttgcactgc aaacggttct     240
tgtgacccat ccgttactcg ccaggcatat gctgacgtga cctttttcgtt cacgcagtat    300
agtaccgatg aggaacgagc ttttgttcgt acagagcttg ctgctctgct cgctagtcct    360
ctgctgatcg atgctattga tcagctgaac ccagcgtatt aatgactgct cattgccggt    420
ggtggctcag ggtcaaaacc cgatccggtt attccggatc caccgattga tccgccgcca    480
gggacaggta gtataccctg tcccttcgca atttggtccc tagaggaggt ttacgagcct    540
cctactaaga accgaccgtg gcctatctat aatgctgttg aactccagcc tcgcgaattt    600
gatgttgccc tcaaagatct tttgggcaat acaaagtggc gtgattggga ttctcggctt    660
agttatacca cgttccgcgg ttgccgtggc aatggttata ttgaccttga tgcgacttat    720
cttgctactg atcaggctat gcgtgatcag aagtatgata ttcgcgaggg caagaaacct    780
ggtgctttcg gtaacattga gcgattcatt tatcttaagt cgataaatgc ttattgctct    840
cttagcgata ttgcggccta tcacgccgat ggcgtgatag ttggcttttg cgcgatccca    900
tccagtggtg gtgccatacc gtttgacttc actaagtttg ataagactaa atgtcctatt    960
caagccgtga tagtcgttcc tcgtgcttag taactaagga tgaaatgcat gtctaag      1017
```

<210> SEQ ID NO 7
<211> LENGTH: 132
<212> TYPE: PRT
<213> ORGANISM: Bacteriophage Q-beta

<400> SEQUENCE: 7

Ala Lys Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

```
Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 8
<211> LENGTH: 132
<212> TYPE: PRT
<213> ORGANISM: Bacteriophage Q-beta

<400> SEQUENCE: 8

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 9
<211> LENGTH: 132
<212> TYPE: PRT
<213> ORGANISM: Bacteriophage Q-beta

<400> SEQUENCE: 9

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

-continued

<210> SEQ ID NO 10
<211> LENGTH: 132
<212> TYPE: PRT
<213> ORGANISM: Bacteriophage Q-beta

<400> SEQUENCE: 10

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 11
<211> LENGTH: 132
<212> TYPE: PRT
<213> ORGANISM: Bacteriophage Q-beta

<400> SEQUENCE: 11

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 12
<211> LENGTH: 131
<212> TYPE: PRT
<213> ORGANISM: Bacteriophage AP205

<400> SEQUENCE: 12

Met Ala Asn Lys Pro Met Gln Pro Ile Thr Ser Thr Ala Asn Lys Ile

```
1               5                   10                  15
Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
                100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 13
<211> LENGTH: 131
<212> TYPE: PRT
<213> ORGANISM: Bacteriophage AP205

<400> SEQUENCE: 13

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
                100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 14
<211> LENGTH: 131
<212> TYPE: PRT
<213> ORGANISM: Bacteriophage AP205

<400> SEQUENCE: 14

Met Ala Asn Lys Pro Met Gln Pro Ile Thr Ser Thr Ala Asp Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
```

```
            50                  55                  60
Cys Ala Asp Ala Cys Val Ile Met Pro Asn Glu Asn Gln Ser Ile Arg
 65                  70                  75                  80

Thr Val Ile Ser Gly Ser Ala Glu Asn Leu Ala Thr Leu Lys Ala Glu
                 85                  90                  95

Trp Glu Thr His Lys Arg Asn Val Asp Thr Leu Phe Ala Ser Gly Asn
                100                 105                 110

Ala Gly Leu Gly Phe Leu Asp Pro Thr Ala Ala Ile Val Ser Ser Asp
            115                 120                 125

Thr Thr Ala
        130

<210> SEQ ID NO 15
<211> LENGTH: 329
<212> TYPE: PRT
<213> ORGANISM: Bacteriophage Q-beta

<400> SEQUENCE: 15

Met Ala Lys Leu Glu Thr Val Thr Leu Gly Asn Ile Gly Lys Asp Gly
  1               5                  10                  15

Lys Gln Thr Leu Val Leu Asn Pro Arg Gly Val Asn Pro Thr Asn Gly
                 20                  25                  30

Val Ala Ser Leu Ser Gln Ala Gly Ala Val Pro Ala Leu Glu Lys Arg
             35                  40                  45

Val Thr Val Ser Val Ser Gln Pro Ser Arg Asn Arg Lys Asn Tyr Lys
         50                  55                  60

Val Gln Val Lys Ile Gln Asn Pro Thr Ala Cys Thr Ala Asn Gly Ser
 65                  70                  75                  80

Cys Asp Pro Ser Val Thr Arg Gln Ala Tyr Ala Asp Val Thr Phe Ser
                 85                  90                  95

Phe Thr Gln Tyr Ser Thr Asp Glu Glu Arg Ala Phe Val Arg Thr Glu
                100                 105                 110

Leu Ala Ala Leu Leu Ala Ser Pro Leu Leu Ile Asp Ala Ile Asp Gln
            115                 120                 125

Leu Asn Pro Ala Tyr Trp Thr Leu Leu Ile Ala Gly Gly Gly Ser Gly
        130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
                180                 185                 190

Val Glu Leu Gln Pro Arg Glu Phe Asp Val Ala Leu Lys Asp Leu Leu
            195                 200                 205

Gly Asn Thr Lys Trp Arg Asp Trp Asp Ser Arg Leu Ser Tyr Thr Thr
        210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
                260                 265                 270

Lys Ser Ile Asn Ala Tyr Cys Ser Leu Ser Asp Ile Ala Ala Tyr His
            275                 280                 285
```

```
Ala Asp Gly Val Ile Val Gly Phe Trp Arg Asp Pro Ser Ser Gly Gly
        290                 295                 300
Ala Ile Pro Phe Asp Phe Thr Lys Phe Asp Lys Thr Lys Cys Pro Ile
305                 310                 315                 320
Gln Ala Val Ile Val Val Pro Arg Ala
                325
```

<210> SEQ ID NO 16
<211> LENGTH: 129
<212> TYPE: PRT
<213> ORGANISM: Bacteriophage R17

<400> SEQUENCE: 16

```
Ala Ser Asn Phe Thr Gln Phe Val Leu Val Asn Asp Gly Gly Thr Gly
1               5                   10                  15
Asn Val Thr Val Ala Pro Ser Asn Phe Ala Asn Gly Val Ala Glu Trp
                20                  25                  30
Ile Ser Ser Asn Ser Arg Ser Gln Ala Tyr Lys Val Thr Cys Ser Val
            35                  40                  45
Arg Gln Ser Ser Ala Gln Asn Arg Lys Tyr Thr Ile Lys Val Glu Val
        50                  55                  60
Pro Lys Val Ala Thr Gln Thr Val Gly Gly Val Glu Leu Pro Val Ala
65                  70                  75                  80
Ala Trp Arg Ser Tyr Leu Asn Met Glu Leu Thr Ile Pro Ile Phe Ala
                85                  90                  95
Thr Asn Ser Asp Cys Glu Leu Ile Val Lys Ala Met Gln Gly Leu Leu
            100                 105                 110
Lys Asp Gly Asn Pro Ile Pro Ser Ala Ile Ala Ala Asn Ser Gly Ile
        115                 120                 125
Tyr
```

<210> SEQ ID NO 17
<211> LENGTH: 130
<212> TYPE: PRT
<213> ORGANISM: Bacteriophage fr

<400> SEQUENCE: 17

```
Met Ala Ser Asn Phe Glu Glu Phe Val Leu Val Asp Asn Gly Gly Thr
1               5                   10                  15
Gly Asp Val Lys Val Ala Pro Ser Asn Phe Ala Asn Gly Val Ala Glu
                20                  25                  30
Trp Ile Ser Ser Asn Ser Arg Ser Gln Ala Tyr Lys Val Thr Cys Ser
            35                  40                  45
Val Arg Gln Ser Ser Ala Asn Asn Arg Lys Tyr Thr Val Lys Val Glu
        50                  55                  60
Val Pro Lys Val Ala Thr Gln Val Gln Gly Gly Val Glu Leu Pro Val
65                  70                  75                  80
Ala Ala Trp Arg Ser Tyr Met Asn Met Glu Leu Thr Ile Pro Val Phe
                85                  90                  95
Ala Thr Asn Asp Asp Cys Ala Leu Ile Val Lys Ala Leu Gln Gly Thr
            100                 105                 110
Phe Lys Thr Gly Asn Pro Ile Ala Thr Ala Ile Ala Ala Asn Ser Gly
        115                 120                 125
Ile Tyr
130
```

<210> SEQ ID NO 18
<211> LENGTH: 130
<212> TYPE: PRT
<213> ORGANISM: Bacteriophage GA

<400> SEQUENCE: 18

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
                20                  25                  30

Leu Ser Asn Asn Ser Arg Ser Gln Ala Tyr Arg Val Thr Ala Ser Tyr
            35                  40                  45

Arg Ala Ser Gly Ala Asp Lys Arg Lys Tyr Ala Ile Lys Leu Glu Val
50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
                100                 105                 110

Lys Val Gly Asn Pro Ile Ala Glu Ala Ile Ser Ser Gln Ser Gly Phe
            115                 120                 125

Tyr Ala
    130

<210> SEQ ID NO 19
<211> LENGTH: 132
<212> TYPE: PRT
<213> ORGANISM: Bacteriophage SP

<400> SEQUENCE: 19

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
                20                  25                  30

Val Ala Ser Leu Ser Glu Ala Gly Ala Val Pro Ala Leu Glu Lys Arg
            35                  40                  45

Val Thr Val Ser Val Ala Gln Pro Ser Arg Asn Arg Lys Asn Phe Lys
50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
                100                 105                 110

Ala Ala Leu Leu Ala Asp Pro Leu Ile Val Asp Ala Ile Asp Asn Leu
            115                 120                 125

Asn Pro Ala Tyr
    130

<210> SEQ ID NO 20
<211> LENGTH: 329
<212> TYPE: PRT
<213> ORGANISM: Bacteriophage

<400> SEQUENCE: 20

Ala Lys Leu Asn Gln Val Thr Leu Ser Lys Ile Gly Lys Asn Gly Asp
1               5                   10                  15

-continued

```
Gln Thr Leu Thr Leu Thr Pro Arg Gly Val Asn Pro Thr Asn Gly Val
             20                  25                  30

Ala Ser Leu Ser Glu Ala Gly Ala Val Pro Ala Leu Glu Lys Arg Val
         35                  40                  45

Thr Val Ser Val Ala Gln Pro Ser Arg Asn Arg Lys Asn Phe Lys Val
 50                  55                  60

Gln Ile Lys Leu Gln Asn Pro Thr Ala Cys Thr Arg Asp Ala Cys Asp
 65                  70                  75                  80

Pro Ser Val Thr Arg Ser Ala Phe Ala Asp Val Thr Leu Ser Phe Thr
                 85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Leu Val Ala Ser Ser Gly Gly Gly Asp
130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
        195                 200                 205

Gly Asn Thr Asn Trp Arg Asn Trp Asp Gln Arg Leu Ser Asp Tyr Asp
    210                 215                 220

Ile Ala Asn Arg Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270

Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
                325

<210> SEQ ID NO 21
<211> LENGTH: 130
<212> TYPE: PRT
<213> ORGANISM: Bacteriophage MS2

<400> SEQUENCE: 21

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
```

```
                    50                  55                  60
Val Pro Lys Val Ala Thr Gln Thr Val Gly Gly Val Glu Leu Pro Val
 65                  70                  75                  80

Ala Ala Trp Arg Ser Tyr Leu Asn Met Glu Leu Thr Ile Pro Ile Phe
                 85                  90                  95

Ala Thr Asn Ser Asp Cys Glu Leu Ile Val Lys Ala Met Gln Gly Leu
                100                 105                 110

Leu Lys Asp Gly Asn Pro Ile Pro Ser Ala Ile Ala Ala Asn Ser Gly
            115                 120                 125

Ile Tyr
    130

<210> SEQ ID NO 22
<211> LENGTH: 133
<212> TYPE: PRT
<213> ORGANISM: Bacteriophage M11

<400> SEQUENCE: 22

Met Ala Lys Leu Gln Ala Ile Thr Leu Ser Gly Ile Gly Lys Lys Gly
  1               5                  10                  15

Asp Val Thr Leu Asp Leu Asn Pro Arg Gly Val Asn Pro Thr Asn Gly
                 20                  25                  30

Val Ala Leu Ser Glu Ala Gly Ala Val Pro Ala Leu Glu Lys Arg
             35                  40                  45

Val Thr Ile Ser Val Ser Gln Pro Ser Arg Asn Arg Lys Asn Tyr Lys
 50                  55                  60

Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ser Asp Val Thr Phe Ser
                 85                  90                  95

Phe Thr Gln Tyr Ser Thr Val Glu Gly Arg Ala Leu Val Arg Thr Glu
                100                 105                 110

Leu Gln Ala Leu Leu Ala Asp Pro Met Leu Val Asn Ala Ile Asp Asn
            115                 120                 125

Leu Asn Pro Ala Tyr
            130

<210> SEQ ID NO 23
<211> LENGTH: 133
<212> TYPE: PRT
<213> ORGANISM: Bacteriophage MX1

<400> SEQUENCE: 23

Met Ala Lys Leu Gln Ala Ile Thr Leu Ser Gly Ile Gly Lys Asn Gly
  1               5                  10                  15

Asp Val Thr Leu Asn Leu Asn Pro Arg Gly Val Asn Pro Thr Asn Gly
                 20                  25                  30

Val Ala Ala Leu Ser Glu Ala Gly Ala Val Pro Ala Leu Glu Lys Arg
             35                  40                  45

Val Thr Ile Ser Val Ser Gln Pro Ser Arg Asn Arg Lys Asn Tyr Lys
 50                  55                  60

Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ala Asp Val Thr Phe Ser
                 85                  90                  95

Phe Thr Gln Tyr Ser Thr Asp Glu Glu Arg Ala Leu Val Arg Thr Glu
```

```
            100                 105                 110
Leu Lys Ala Leu Leu Ala Asp Pro Met Leu Ile Asp Ala Ile Asp Asn
            115                 120                 125
Leu Asn Pro Ala Tyr
            130

<210> SEQ ID NO 24
<211> LENGTH: 330
<212> TYPE: PRT
<213> ORGANISM: Bacteriophage NL95

<400> SEQUENCE: 24

Met Ala Lys Leu Asn Lys Val Thr Leu Thr Gly Ile Gly Lys Ala Gly
1               5                   10                  15
Asn Gln Thr Leu Thr Leu Thr Pro Arg Gly Val Asn Pro Thr Asn Gly
            20                  25                  30
Val Ala Ser Leu Ser Glu Ala Gly Ala Val Pro Ala Leu Glu Lys Arg
        35                  40                  45
Val Thr Val Ser Val Ala Gln Pro Ser Arg Asn Arg Lys Asn Tyr Lys
    50                  55                  60
Val Gln Ile Lys Leu Gln Asn Pro Thr Ala Cys Thr Lys Asp Ala Cys
65                  70                  75                  80
Asp Pro Ser Val Thr Arg Ser Gly Ser Arg Asp Val Thr Leu Ser Phe
                85                  90                  95
Thr Ser Tyr Ser Thr Glu Arg Glu Arg Ala Leu Ile Arg Thr Glu Leu
            100                 105                 110
Ala Ala Leu Leu Lys Asp Asp Leu Ile Val Asp Ala Ile Asp Asn Leu
        115                 120                 125
Asn Pro Ala Tyr Trp Ala Ala Leu Leu Ala Ala Ser Pro Gly Gly Gly
    130                 135                 140
Asn Asn Pro Tyr Pro Gly Val Pro Asp Ser Pro Asn Val Lys Pro Pro
145                 150                 155                 160
Gly Gly Thr Gly Thr Tyr Arg Cys Pro Phe Ala Cys Tyr Arg Arg Gly
                165                 170                 175
Glu Leu Ile Thr Glu Ala Lys Asp Gly Ala Cys Ala Leu Tyr Ala Cys
            180                 185                 190
Gly Ser Glu Ala Leu Val Glu Phe Glu Tyr Ala Leu Glu Asp Phe Leu
        195                 200                 205
Gly Asn Glu Phe Trp Arg Asn Trp Asp Gly Arg Leu Ser Lys Tyr Asp
    210                 215                 220
Ile Glu Thr His Arg Arg Cys Arg Gly Asn Gly Tyr Val Asp Leu Asp
225                 230                 235                 240
Ala Ser Val Met Gln Ser Asp Glu Tyr Val Leu Ser Gly Ala Tyr Asp
                245                 250                 255
Val Val Lys Met Gln Pro Pro Gly Thr Phe Asp Ser Pro Arg Tyr Tyr
            260                 265                 270
Leu His Leu Met Asp Gly Ile Tyr Val Asp Leu Ala Glu Val Thr Ala
        275                 280                 285
Tyr Arg Ser Tyr Gly Met Val Ile Gly Phe Trp Thr Asp Ser Lys Ser
    290                 295                 300
Pro Gln Leu Pro Thr Asp Phe Thr Arg Phe Asn Arg His Asn Cys Pro
305                 310                 315                 320
Val Gln Thr Val Ile Val Ile Pro Ser Leu
                325                 330
```

<210> SEQ ID NO 25
<211> LENGTH: 129
<212> TYPE: PRT
<213> ORGANISM: Bacteriophage f2

<400> SEQUENCE: 25

```
Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr
```

<210> SEQ ID NO 26
<211> LENGTH: 128
<212> TYPE: PRT
<213> ORGANISM: Bacteriophage PP7

<400> SEQUENCE: 26

```
Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125
```

<210> SEQ ID NO 27
<211> LENGTH: 4586
<212> TYPE: DNA
<213> ORGANISM: artificial sequence
<220> FEATURE:
<223> OTHER INFORMATION: Cloning Vector - chemically synthesized

<400> SEQUENCE: 27

```
ttctgtttcc tgtgtgaaat tgttatccgc tcacaattcc acacattata cgagccgatg      60
attaattgtc aacagctcat ttcagaatat ttgccagaac cgttatgatg tcggcgcaaa     120
```

-continued

```
aaacattatc cagaacggga gtgcgccttg agcgacacga attatgcagt gatttacgac    180
ctgcacagcc ataccacagc ttccgatggc tgcctgacgc cagaagcatt ggtgcaccgt    240
gcagtcgata agctccggat cctctacgcc ggacgcatcg tggccggcat caccggcgcc    300
acaggtgcgg ttgctggcgc ctatatcgcc gacatcaccg atggggaaga tcgggctcgc    360
cacttcgggc tcatgagcgc ttgtttcggc gtgggtatgg tggcaggccc cgtggccggg    420
ggactgttgg cgccatctc cttgcatgca ccattccttg cggcggcggt gctcaacggc     480
ctcaacctac tactgggctg cttcctaatg caggagtcgc ataagggaga gcgtcgaccg    540
atgcccttga gagccttcaa cccagtcagc tccttccggt gggcgcgggg catgactatc    600
gtcgccgcac ttatgactgt cttctttatc atgcaactcg taggacaggt gccggcagcg    660
ctctgggtca ttttcggcga ggaccgcttt cgctggagcg cgacgatgat cggcctgtcg    720
cttgcggtat tcggaatctt gcacgccctc gctcaagcct tcgtcactgg tcccgccacc    780
aaacgtttcg gcgagaagca ggccattatc gccggcatgg cggccgacgc gctgggctac    840
gtcttgctgg cgttcgcgac gcgaggctgg atggccttcc ccattatgat tcttctcgct    900
tccggcggca tcgggatgcc cgcgttgcag gccatgctgt ccaggcaggt agatgacgac    960
catcagggac agcttcaagg atcgctcgcg gctcttacca gcctaacttc gatcactgga    1020
ccgctgatcg tcacggcgat ttatgccgcc tcggcgagca catggaacgg gttggcatgg    1080
attgtaggcg ccgccctata ccttgtctgc ctccccgcgt gcgtcgcgg tgcatggagc     1140 cgggccacct cgacctgaat ggaagccggc ggcacctcgc taacggattc accactccaa    1200
gaattggagc caatcaattc ttgcggagaa ctgtgaatgc gcaaaccaac ccttggcaga    1260
acatatccat cgcgtccgcc atctccagca gccgcacgcg cgcatctcg ggcagcgttg     1320 ggtcctggcc acgggtgcgc atgatcgtgc tcctgtcgtt gaggacccgg ctaggctggc    1380
ggggttgcct tactggttag cagaatgaat caccgatacg cgagcgaacg tgaagcgact    1440
gctgctgcaa acgtctgcg acctgagcaa caacatgaat ggtcttcggt ttccgtgttt     1500
cgtaaagtct ggaaacgcgg aagtcagcgc cctgcaccat tatgttccgg atctgcatcg    1560
caggatgctg ctggctaccc tgtggaacac ctacatctgt attaacgaag cgctggcatt    1620
gaccctgagt gattttctc tggtcccgcc gcatccatac cgccagttgt ttaccctcac     1680
aacgttccag taaccgggca tgttcatcat cagtaacccg tatcgtgagc atcctctctc    1740
gtttcatcgg tatcattacc cccatgaaca gaaattcccc cttacacgga ggcatcaagt    1800
gaccaaacag gaaaaaaccg cccttaacat ggcccgcttt atcagaagcc agacattaac    1860
gcttctggag aaactcaacg agctggacgc ggatgaacag gcagacatct gtgaatcgct    1920
tcacgaccac gctgatgagc tttaccgcag ctgcctcgcg cgtttcggtg atgacggtga    1980
aaacctctga cacatgcagc tcccggagac ggtcacagct tgtctgtaag cggatgccgg    2040
gagcagacaa gcccgtcagg gcgcgtcagc gggtgttggc gggtgtcggg gcgcagccat    2100
gacccagtca cgtagcgata gcggagtgta tactggctta actatgcggc atcagagcag    2160
attgtactga gagtgcacca tatgcggtgt gaaataccgc acagatgcgt aaggagaaaa    2220
taccgcatca ggcgctcttc cgcttcctcg ctcactgact cgctgcgctc ggtcgttcgg    2280
ctgcggcgag cggtatcagc tcactcaaag gcggtaatac ggttatccac agaatcaggg    2340
gataacgcag gaaagaacat gtgagcaaaa ggccagcaaa aggccaggaa ccgtaaaaag    2400
gccgcgttgc tggcgttttt ccataggctc cgcccccctg acgagcatca caaaaatcga    2460
```

-continued

```
cgctcaagtc agaggtggcg aaacccgaca ggactataaa gataccaggc gtttccccct    2520
ggaagctccc tcgtgcgctc tcctgttccg accctgccgc ttaccggata cctgtccgcc    2580
tttctcccct tcgggaagcgt ggcgctttct catagctcac gctgtaggta tctcagttcg   2640
gtgtaggtcg ttcgctccaa gctgggctgt gtgcacgaac cccccgttca gcccgaccgc    2700
tgcgccttat ccggtaacta tcgtcttgag tccaacccgg taagacacga cttatcgcca    2760
ctggcagcag ccactggtaa caggattagc agagcgaggt atgtaggcgg tgctacagag    2820
ttcttgaagt ggtggcctaa ctacggctac actagaagga cagtatttgg tatctgcgct    2880
ctgctgaagc cagttacctt cggaaaaaga gttggtagct cttgatccgg caaacaaacc    2940
accgctggta gcggtggttt ttttgtttgc aagcagcaga ttacgcgcag aaaaaaagga    3000
tctcaagaag atcctttgat cttttctacg ggtctgacg ctcagtggaa cgaaaactca     3060
cgttaaggga ttttggtcat gagattatca aaaggatct tcacctagat ccttttaaat     3120
taaaaatgaa gttttaaatc aatctaaagt atatatgagt aaacttggtc tgacagttac    3180
caatgcttaa tcagtgaggc acctatctca gcgatctgtc tatttcgttc atccatagtt    3240
gcctgactcc ccgtcgtgta gataactacg atacgggagg gcttaccatc tggccccagt    3300
gctgcaatga taccgcgaga cccacgctca ccggctccag atttatcagc aataaaccag    3360
ccagccggaa gggccgagcg cagaagtggt cctgcaactt tatccgcctc catccagtct    3420
attaattgtt gccgggaagc tagagtaagt agttcgccag ttaatagttt gcgcaacgtt    3480
gttgccattg ctacaggcat cgtggtgtca cgctcgtcgt ttggtatggc ttcattcagc    3540
tccggttccc aacgatcaag gcgagttaca tgatccccca tgttgtgcaa aaaagcggtt    3600
agctccttcg gtcctccgat cgttgtcaga agtaagttgg ccgcagtgtt atcactcatg    3660
gttatggcag cactgcataa ttctcttact gtcatgccat ccgtaagatg cttttctgtg    3720
actggtgagt actcaaccaa gtcattctga gaatagtgta tgcggcgacc gagttgctct    3780
tgcccggcgt caacacggga taataccgcg ccacatagca gaactttaaa agtgctcatc    3840
attggaaaac gttcttcggg gcgaaaactc tcaaggatct taccgctgtt gagatccagt    3900
tcgatgtaac ccactcgtgc acccaactga tcttcagcat cttttacttt caccagcgtt    3960
tctgggtgag caaaaacagg aaggcaaaat gccgcaaaaa agggaataag ggcgacacgg    4020
aaatgttgaa tactcatact cttccttttt caatattatt gaagcattta tcagggttat    4080
tgtctcatga gcggatacat atttgaatgt atttagaaaa ataaacaaaa gagtttgtag    4140
aaacgcaaaa aggccatccg tcaggatggc cttctgctta atttgatgcc tggcagttta    4200
tggcgggcgt cctgcccgcc accctccggg ccgttgcttc gcaacgttca aatccgctcc    4260
cggcggattt gtcctactca ggagagcgtt caccgacaaa caacagataa aacgaaaggc    4320
ccagtctttc gactgagcct ttcgttttat ttgatgcctg gcagttccct actctcgcat    4380
ggggagaccc cacactacca tcggcgctac ggcgtttcac ttctgagttc ggcatggggt    4440
caggtgggac caccgcgcta ctgccgccag gcaaattctg ttttatcaga ccgcttctgc    4500
gttctgattt aatctgtatc aggctgaaaa tcttctctca tccgccaaaa cagaagcttg    4560
gctgcaggtc gacggatccc cgggaa                                         4586
```

<210> SEQ ID NO 28
<211> LENGTH: 425
<212> TYPE: DNA
<213> ORGANISM: artificial sequence
<220> FEATURE:
<223> OTHER INFORMATION: Terminator Sequence - chemically synthesized

<400> SEQUENCE: 28

```
ctgttttggc ggatgagaga agattttcag cctgatacag attaaatcag aacgcagaag      60
cggtctgata aaacagaatt tgcctggcgg cagtagcgcg gtggtcccac ctgaccccat     120
gccgaactca gaagtgaaac gccgtagcgc cgatggtagt gtggggtctc cccatgcgag    180
agtagggaac tgccaggcat caaataaaac gaaaggctca gtcgaaagac tgggcctttc    240
gttttatctg ttgtttgtcg gtgaacgctc tcctgagtag gacaaatccg ccgggagcgg    300
atttgaacgt tgcgaagcaa cggcccggag ggtggcgggc aggacgcccg ccataaactg    360
ccaggcatca aattaagcag aaggccatcc tgacggatgg cctttttgcg tttctacaaa    420
ctctt                                                                  425
```

<210> SEQ ID NO 29
<211> LENGTH: 816
<212> TYPE: DNA
<213> ORGANISM: artificial sequence
<220> FEATURE:
<223> OTHER INFORMATION: Resistance gene - chemically synthesized

<400> SEQUENCE: 29

```
ttagaaaaac tcatcgagca tcaaatgaaa ctgcaattta ttcatatcag gattatcaat      60
accatatttt tgaaaaagcc gtttctgtaa tgaaggagaa aactcaccga ggcagttcca    120
taggatggca agatcctggt atcggtctgc gattccgact cgtccaacat caatacaacc    180
tattaatttc ccctcgtcaa aaataaggtt atcaagtgag aaatcaccat gagtgacgac    240
tgaatccggt gagaatggca aaagcttatg catttctttc cagacttgtt caacaggcca    300
gccattacgc tcgtcatcaa aatcactcgc atcaaccaaa ccgttattca ttcgtgattg    360
cgcctgagcg agacgaaata cgcgatcgct gttaaaagga caattacaaa caggaatcga    420
atgcaaccgg cgcaggaaca ctgccagcgc atcaacaata ttttcacctg aatcaggata    480
ttcttctaat acctggaatg ctgttttccc ggggatcgca gtggtgagta accatgcatc    540
atcaggagta cggataaaat gcttgatggt cggaagaggc ataaattccg tcagccagtt    600
tagtctgacc atctcatctg taacatcatt ggcaacgcta cctttgccat gtttcagaaa    660
caactctggc gcatcgggct tcccatacaa tcgatagatt gtcgcacctg attgcccgac    720
attatcgcga gcccatttat acccatataa atcagcatcc atgttggaat ttaatcgcgg    780
cctcgagcaa gacgtttccc gttgaatatg gctcat                                 816
```

<210> SEQ ID NO 30
<211> LENGTH: 4963
<212> TYPE: DNA
<213> ORGANISM: artificial sequence
<220> FEATURE:
<223> OTHER INFORMATION: Plasmid - chemically synthesized

<400> SEQUENCE: 30

```
ggctgtgcag gtcgtaaatc actgcataat tcgtgtcgct caaggcgcac tcccgttctg      60
gataatgttt tttgcgccga catcataacg gttctggcaa atattctgaa atgagctgtt    120
gacaattaat catcggctcg tataatgtgt ggaattgtga gcggataaca atttcacaca    180
ggaaacagaa ttctaaggag gaaaaaaaaa tggcaaataa gccaatgcaa ccgatcacat    240
ctacagcaaa taaaattgtg tggtcggatc caactcgttt atcaactaca ttttcagcaa    300
gtctgttacg ccaacgtgtt aaagttggta tagccgaact gaataatgtt tcaggtcaat    360
```

```
atgtatctgt ttataagcgt cctgcaccta aaccggaagg ttgtgcagat gcctgtgtca    420
ttatgccgaa tgaaaaccaa tccattcgca cagtgatttc agggtcagcc gaaaacttgg    480
ctaccttaaa agcagaatgg gaaactcaca aacgtaacgt tgacacactc ttcgcgagcg    540
gcaacgccgg tttgggtttc cttgacccta ctgcggctat cgtatcgtct gatactactg    600
cttaatgaag cttggctgtt ttggcggatg agagaagatt ttcagcctga tacagattaa    660
atcagaacgc agaagcggtc tgataaaaca gaatttgcct ggcggcagta gcgcggtggt    720
cccacctgac cccatgccga actcagaagt gaaacgccgt agcgccgatg gtagtgtggg    780
gtctccccat gcgagagtag ggaactgcca ggcatcaaat aaaacgaaag gctcagtcga    840
aagactgggc ctttcgtttt atctgttgtt tgtcggtgaa cgctctcctg agtaggacaa    900
atccgccggg agcggatttg aacgttgcga agcaacggcc cggagggtgg cgggcaggac    960
gcccgccata aactgccagg catcaaatta agcagaaggc catcctgacg gatggccttt    1020
ttgcgtttct acaaactctt tgtttattt ttctagagcc acgttgtgtc tcaaaatctc    1080
tgatgttaca ttgcacaaga taaaaatata tcatcatgaa caataaaact gtctgcttac    1140
ataaacagta atacaaggag tgttatgagc catattcaac gggaaacgtc ttgctcgagg    1200
ccgcgattaa attccaacat ggatgctgat ttatatggga taaatgggc tcgcgataat    1260
gtcgggcaat caggtgcgac aatctatcga ttgtatggga agcccgatgc gccagagttg    1320
tttctgaaac atggcaaagg tagcgttgcc aatgatgtta cagatgagat ggtcagacta    1380
aactggctga cggaatttat gcctcttccg accatcaagc attttatccg tactcctgat    1440
gatgcatggt tactcaccac tgcgatcccc gggaaaacag cattccaggt attagaagaa    1500
tatcctgatt caggtgaaaa tattgttgat gcgctggcag tgttcctgcg ccggttgcat    1560
tcgattcctg tttgtaattg tccttttaac agcgatcgcg tatttcgtct cgctcaggcg    1620
caatcacgaa tgaataacgg tttggttgat gcgagtgatt ttgatgacga gcgtaatggc    1680
tggcctgttg aacaagtctg gaaagaaatg cataagcttt tgccattctc accggattca    1740
gtcgtcactc atggtgattt ctcacttgat aaccttattt ttgacgaggg gaaattaata    1800
ggttgtattg atgttggacg agtcggaatc gcagaccgat accaggatct tgccatccta    1860
tggaactgcc tcggtgagtt ttctccttca ttacagaaac ggcttttttca aaaatatggt    1920
attgataatc ctgatatgaa taaattgcag tttcatttga tgctcgatga gttttttctaa    1980
acgcgtgacc aagtttactc atatgtactt tagattgatt taaaacttca ttttttaattt    2040
aaaaggatct aggtgaagat cctttttgat aatctcatga ccaaaatccc ttaacgtgag    2100
ttttcgttcc actgagcgtc agaccccgta gaaaagatca aaggatcttc ttgagatcct    2160
ttttttctgc gcgtaatctg ctgcttgcaa acaaaaaaac caccgctacc agcggtggtt    2220
tgtttgccgg atcaagagct accaactctt tttccgaagg taactggctt cagcagagcg    2280
cagataccaa atactgtcct tctagtgtag ccgtagttag gccaccactt caagaactct    2340
gtagcaccgc ctacatacct cgctctgcta atcctgttac cagtggctgc tgccagtggc    2400
gataagtcgt gtcttaccgg gttggactca agacgatagt taccggataa ggcgcagcgg    2460
tcgggctgaa cggggggttc gtgcacacag cccagcttgg agcgaacgac ctacaccgaa    2520
ctgagatacc tacagcgtga gctatgagaa agcgccacgc ttcccgaagg gagaaaggcg    2580
gacaggtatc cggtaagcgg cagggtcgga acaggagagc gcacgaggga gctcccaggg    2640
ggaaacgcct ggtatcttta tagtcctgtc gggtttcgcc acctctgact tgagcgtcga    2700
tttttgtgat gctcgtcagg gggcggagc ctatggaaaa acgccagcaa cgcggccttt    2760
```

-continued

```
ttacggttcc tggccttttg ctggccttttt gctcacatgt tctttcctgc gttatccct      2820 gattctgtgg ataaccgtat taccgccttt gagtgagctg ataccgctcg ccgcagccga      2880
acgaccgagc gcagcgagtc agtgagcgag gaagcggaag agcgcctgat gcggtatttt      2940
ctccttacgc atctgtgcgg tatttcacac cgcatatggt gcactctcag tacaatctgc      3000
tctgatgccg catagttaag ccagtataca ctccgctatc gctacgtgac tgggtcatgg      3060
ctgcgccccg acaccgcca acaccgctg acgcgcctg acgggcttgt ctgctccgg         3120 catccgctta cagacaagct gtgaccgtct ccgggagctg catgtgtcag aggttttcac      3180
cgtcatcacc gaaacgcgcg aggcagctgc ggtaaagctc atcagcgtgg tcgtgaagcg      3240
attcacagat gtctgcctgt tcatccgcgt ccagctcgtt gagtttctcc agaagcgtta      3300
atgtctggct tctgataaag cgggccatgt taagggcggt tttttcctgt ttggtcactg      3360
atgcctccgt gtaaggggga tttctgttca tgggggtaat gataccgatg aaacgagaga      3420
ggatgctcac gatacgggtt actgatgatg aacatgcccg gttactggaa cgttgtgagg      3480
gtaaacaact ggcggtatgg atgcggcggg accagagaaa aatcactcag ggtcaatgcc      3540
agcgcttcgt taatacagat gtaggtgttc cacagggtag ccagcagcat cctgcgatgc      3600
agatccggaa cataatggtg cagggcgctg acttccgcgt ttccagactt tacgaaacac      3660
ggaaaccgaa gaccattcat gttgttgctc aggtcgcaga cgttttgcag cagcagtcgc      3720
ttcacgttcg ctcgcgtatc ggtgattcat tctgctaacc agtaaggcaa ccccgccagc      3780
ctagccgggt cctcaacgac aggagcacga tcatgcgcac ccgtggccag gacccaacgc      3840
tgcccgagat gcgccgcgtg cggctgctgg agatggcgga cgcgatggat atgttctgcc      3900
aagggttggt ttgcgcattc acagttctcc gcaagaattg attggctcca attcttggag      3960
tggtgaatcc gttagcgagg tgccgccggc ttccattcag gtcgaggtgg cccggctcca      4020
tgcaccgcga cgcaacgcgg ggaggcagac aaggtatagg gcggcgccta caatccatgc      4080
caacccgttc catgtgctcg ccgaggcggc ataaatcgcc gtgacgatca gcggtccaat      4140
gatcgaagtt aggctggtaa gagccgcgag cgatccttga agctgtccct gatggtcgtc      4200
atctacctgc ctggacagca tggcctgcaa cgcgggcatc ccgatgccgc cggaagcgag      4260
aagaatcata tgggggaagg ccatccagcc tcgcgtcgcg aacgccagca agacgtagcc      4320
cagcgcgtcg gccgccatgc cggcgataat ggcctgcttc tcgccgaaac gtttggtggc      4380
gggaccagtg acgaaggctt gagcgagggc gtgcaagatt ccgaataccg caagcgacag      4440
gccgatcatc gtcgcgctcc agcgaaagcg gtcctcgccg aaaatgaccc agagcgctgc      4500
cggcacctgt cctacgagtt gcatgataaa gaagacagtc ataagtgcgg cgacgatagt      4560
catgccccgc gcccaccgga aggagctgac tgggttgaag gctctcaagg gcatcggtcg      4620
acgctctccc ttatgcgact cctgcattag gaagcagccc agtagtaggt tgaggccgtt      4680
gagcaccgcc gccgcaagga atggtgcatg caaggagatg gcgcccaaca gtccccggc      4740 cacggggcct gccaccatac ccacgccgaa acaagcgctc atgagcccga agtggcgagc      4800
ccgatcttcc ccatcggtga tgtcggcgat ataggcgcca gcaaccgcac ctgtggcgcc      4860
ggtgatgccg gccacgatgc gtccggcgta gaggatccgg gcttatcgac tgcacggtgc      4920
accaatgctt ctggcgtcag gcagccatcg gaagctgtgg tat                       4963
```

<210> SEQ ID NO 31
<211> LENGTH: 6
<212> TYPE: DNA

```
<213> ORGANISM: artificial sequence
<220> FEATURE:
<223> OTHER INFORMATION: Stop Codon - chemically synthesized

<400> SEQUENCE: 31 tgaaca                                                                      6

<210> SEQ ID NO 32
<211> LENGTH: 6
<212> TYPE: DNA
<213> ORGANISM: artificial sequence
<220> FEATURE:
<223> OTHER INFORMATION: Stop Codon - chemically synthesized

<400> SEQUENCE: 32 taatga                                                                      6

<210> SEQ ID NO 33
<211> LENGTH: 4525
<212> TYPE: DNA
<213> ORGANISM: artificial sequence
<220> FEATURE:
<223> OTHER INFORMATION: Plasmid - chemically synthesized

<400> SEQUENCE: 33
tcgcgcgttt cggtgatgac ggtgaaaacc tctgacacat gcagctcccg gagacggtca         60
cagcttgtct gtaagcggat gccgggagca gacaagcccg tcaggcgcg tcagcgggtg        120 ttggcgggtg tcggggctgg cttaactatg cggcatcaga gcagattgta ctgagagtgc        180
accatatgcg gtgtgaaata ccgcacagat gcgtaaggag aaaataccgc atcaggcgcc        240
attcgccatt caggctgcgc aactgttggg aagggcgatc ggtgcgggcc tcttcgctat        300
tacgccagct ggcgaaaggg ggatgtgctg caaggcgatt aagttgggta acgccagggt        360
tttcccagtc acgacgttgt aaaacgacgg ccagtgaatt cagacatgca tttcatcctt        420
agttactaag cacgaggaac gactatcacg gcttgaatag gcatttagt cttatcaaac         480 ttagtgaagt caaacggtat ggcaccacca ctggatggat cgcgccaaaa gccaactatc        540
acgccatcgg cgtgataggc cgcaatatcg ctaagagagc aataagcatt tatcgactta        600
agataaatga atcgctcaat gttaccgaaa gcaccaggtt tcttgccctc gcgaatatca        660
tacttctgat cacgcatagc ctgatcagta gcaagataag tcgcatcaag gtcaatataa        720
ccattgccac ggcaaccgcg gaacgtggta taactaagcc gagaatccca atcacgccac        780
tttgtattgc ccaaaagatc tttgagggca acatcaaatt cgcgaggctg gagttcaaca        840
gcattataga taggccacgg tcggttctta gtaggaggct cgtaaacctc tctagggac         900 caaattgcga agggacaggt atacttacct gtccctggcg gcggatcaat cggtggatcc        960
ggaataaccg gatcgggttt tgaccctgag ccaccaccgg caatgagcag tcattaatac       1020
gctgggttca gctgatcaat agcatcgatc agcagaggac tagcgagcag agcagcaagc       1080
tctgtacgaa caaaagctcg ttcctcatcg gtactatact gcgtgaacga aaaggtcacg       1140
tcagcatatg cctggcgagt aacggatggg tcacaagaac cgtttgcagt gcaagcggtc       1200
gggttctgga tcttaacctg gaccttgtag ttcttacgat tgcgagaagg ctgagatacc       1260
gaaacggtaa cacgcttctc cagcgcagga actgcacccg cttgtgaaag cgaggcaacg       1320
ccgttagtgg gatttacccc acgcggattg aggaccagag tttgtttccc atctttcccg       1380
atgttaccta aagtaacagt ctctaatttt gccatcgttt tttacctcct tctagagtca       1440
ttatggtttt gccatacatc agtatggtgt agcagcactt attataatct ttattgcctc       1500
```

```
ttaaaactta atccacatca aaactcaaat acttttaacc ccagcgtcct gtaagctctg    1560
cattaatgaa tcggccaacg cgcggggaga ggcggtttgc gtattgggcg ctcttccgct    1620
tcctcgctca ctgactcgct gcgctcggtc gttcggctgc ggcgagcggt atcagctcac    1680
tcaaaggcgg taatacggtt atccacagaa tcaggggata acgcaggaaa gaacatgtga    1740
gcaaaaggcc agcaaaaggc caggaaccgt aaaaaggccg cgttgctggc gtttttccat    1800
aggctccgcc cccctgacga gcatcacaaa aatcgacgct caagtcagag gtggcgaaac    1860
ccgacaggac tataaagata ccaggcgttt ccccctggaa gctccctcgt gcgctctcct    1920
gttccgaccc tgccgcttac cggatacctg tccgcctttc tcccttcggg aagcgtggcg    1980
ctttctcata gctcacgctg taggtatctc agttcggtgt aggtcgttcg ctccaagctg    2040
ggctgtgtgc acgaaccccc cgttcagccc gaccgctgcg ccttatccgg taactatcgt    2100
cttgagtcca acccggtaag acacgactta tcgccactgg cagcagccac tggtaacagg    2160
attagcagag cgaggtatgt aggcggtgct acagagttct tgaagtggtg cctaactac    2220 ggctacacta gaagaacagt atttggtatc tgcgctctgc tgaagccagt taccttcgga    2280
aaaagagttg gtagctcttg atccggcaaa caaaccaccg ctggtagcgg tggtttttt    2340 gtttgcaagc agcagattac gcgcagaaaa aaaggatctc aagaagatcc tttgatcttt    2400
tctacggggt ctgacgctca gtggaacgaa aactcacgtt aagggatttt ggtcatgaga    2460
ttatcaaaaa ggatcttcac ctagatcctt ttaaattaaa aatgaagttt taaatcaatc    2520
taaagtatat atgagtaaac ttggtctgac agttaccaat gcttaatcag tgaggcacct    2580
atctcagcga tctgtctatt tcgttcatcc atagttgcct gactccccgt cgtgtagata    2640
actacgatac gggagggctt accatctggc cccagtgctg caatgatacc gcgagaccca    2700
cgctcaccgg ctccagattt atcagcaata aaccagccag ccggaagggc cgagcgcaga    2760
agtggtcctg caactttatc cgcctccatc cagtctatta attgttgccg ggaagctaga    2820
gtaagtagtt cgccagttaa tagtttgcgc aacgttgttg ccattgctac aggcatcgtg    2880
gtgtcacgct cgtcgtttgg tatggcttca ttcagctccg gttcccaacg atcaaggcga    2940
gttacatgat cccccatgtt gtgcaaaaaa gcggttagct ccttcggtcc tccgatcgtt    3000
gtcagaagta agttggccgc agtgttatca ctcatggtta tggcagcact gcataattct    3060
cttactgtca tgccatccgt aagatgcttt tctgtgactg gtgagtgggg ggggggggcg    3120
ctgaggtctg cctcgtgaag aaggtgttgc tgactcatac caggcctgaa tcgccccatc    3180
atccagccag aaagtgaggg agccacggtt gatgagagct ttgttgtagg tggaccagtt    3240
ggtgattttg aacttttgct ttgccacgga acggtctgcg ttgtcgggaa gatgcgtgat    3300
ctgatccttc aactcagcaa aagttcgatt tattcaacaa agccgccgtc ccgtcaagtc    3360
agcgtaatgc tctgccagtg ttacaaccaa ttaaccaatt ctgattagaa aaactcatcg    3420
agcatcaaat gaaactgcaa tttattcata tcaggattat caataccata tttttgaaaa    3480
agccgtttct gtaatgaagg agaaaactca ccgaggcagt tccataggat ggcaagatcc    3540
tggtatcggt ctgcgattcc gactcgtcca acatcaatac aacctattaa tttcccctcg    3600
tcaaaaataa ggttatcaag tgagaaatca ccatgagtga cgactgaatc cggtgagaat    3660
ggcaaaagct tatgcatttc tttccagact tgttcaacag gccagccatt acgctcgtca    3720
tcaaaatcac tcgcatcaac caaaccgtta ttcattcgtg attgcgcctg agcgagacga    3780
aatacgcgat cgctgttaaa aggacaatta caaacaggaa tcgaatgcaa ccggcgcagg    3840
```

| aacactgcca gcgcatcaac aatattttca cctgaatcag gatattcttc taatacctgg | 3900 |
| aatgctgttt tcccggggat cgcagtggtg agtaaccatg catcatcagg agtacggata | 3960 |
| aaatgcttga tggtcggaag aggcataaat tccgtcagcc agtttagtct gaccatctca | 4020 |
| tctgtaacat cattggcaac gctacctttg ccatgtttca gaaacaactc tggcgcatcg | 4080 |
| ggcttcccat acaatcgata gattgtcgca cctgattgcc cgacattatc gcgagcccat | 4140 |
| ttatacccat ataaatcagc atccatgttg gaatttaatc gcggcctcga gcaagacgtt | 4200 |
| tcccgttgaa tatggctcat aacacccctt gtattactgt ttatgtaagc agacagtttt | 4260 |
| attgttcatg atgatatatt tttatcttgt gcaatgtaac atcagagatt ttgagacaca | 4320 |
| acgtggcttt ccccccccccc ccattattga agcatttatc agggttattg tctcatgagc | 4380 |
| ggatacatat ttgaatgtat ttagaaaaat aaacaaatag gggttccgcg cacatttccc | 4440 |
| cgaaaagtgc cacctgacgt ctaagaaacc attattatca tgacattaac ctataaaaat | 4500 |
| aggcgtatca cgaggccctt tcgtc | 4525 |

<210> SEQ ID NO 34
<211> LENGTH: 56
<212> TYPE: DNA
<213> ORGANISM: artificial sequence
<220> FEATURE:
<223> OTHER INFORMATION: Primer Sequence - chemically synthesized

<400> SEQUENCE: 34
gcgcgcgaat tcaggaggta aaaaacgatg gcaaaattag agactgttac tttagg         56

<210> SEQ ID NO 35
<211> LENGTH: 33
<212> TYPE: DNA
<213> ORGANISM: artificial sequence
<220> FEATURE:
<223> OTHER INFORMATION: Primer Sequence - chemically synthesized

<400> SEQUENCE: 35
gcatgcaagc ttagacatgc atttcatcct tag                                  33

<210> SEQ ID NO 36
<211> LENGTH: 57
<212> TYPE: DNA
<213> ORGANISM: artificial sequence
<220> FEATURE:
<223> OTHER INFORMATION: Primer Sequence - chemically synthesized

<400> SEQUENCE: 36
gcgcgcgaat tctaaggagg aaaaaaaaat ggcaaaatta gagactgtta ctttagg        57

<210> SEQ ID NO 37
<211> LENGTH: 3914
<212> TYPE: DNA
<213> ORGANISM: artificial sequence
<220> FEATURE:
<223> OTHER INFORMATION: Cloning Vector - chemically synthesized

<400> SEQUENCE: 37

| tcgcgcgttt cggtgatgac ggtgaaaacc tctgacacat gcagctcccg gagacggtca | 60 |
| cagcttgtct gtaagcggat gccggagcag acaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |

```
tacgccagct ggcgaaaggg ggatgtgctg caaggcgatt aagttgggta acgccagggt      360
tttcccagtc acgacgttgt aaaacgacgg ccagtgaatt ccccggatcc gtcgacctgc      420
aggggggggg gggcgctgag gtctgcctcg tgaagaaggt gttgctgact cataccaggc      480
ctgaatcgcc ccatcatcca gccagaaagt gagggagcca cggttgatga gagctttgtt      540
gtaggtggac cagttggtga ttttgaactt ttgctttgcc acggaacggt ctgcgttgtc      600
gggaagatgc gtgatctgat ccttcaactc agcaaaagtt cgatttattc aacaaagccg      660
ccgtcccgtc aagtcagcgt aatgctctgc cagtgttaca accaattaac caattctgat      720
tagaaaaact catcgagcat caaatgaaac tgcaatttat tcatatcagg attatcaata      780
ccatattttt gaaaaagccg tttctgtaat gaaggagaaa actcaccgag gcagttccat      840
aggatggcaa gatcctggta tcggtctgcg attccgactc gtccaacatc aatacaacct      900
attaatttcc cctcgtcaaa ataaggttta caagtgagaa atcaccatg agtgacgact      960 gaatccggtg agaatggcaa aagcttatgc atttctttcc agacttgttc aacaggccag     1020
ccattacgct cgtcatcaaa atcactcgca tcaaccaaac cgttattcat tcgtgattgc     1080
gcctgagcga gacgaaatac gcgatcgctg ttaaaaggac aattacaaac aggaatcgaa     1140
tgcaaccggc gcaggaacac tgccagcgca tcaacaatat tttcacctga atcaggatat     1200
tcttctaata cctggaatgc tgttttcccg gggatcgcag tggtgagtaa ccatgcatca     1260
tcaggagtac ggataaaatg cttgatggtc ggaagaggca taaattccgt cagccagttt     1320
agtctgacca tctcatctgt aacatcattg gcaacgctac ctttgccatg tttcagaaac     1380
aactctggcg catcgggctt cccatacaat cgatagattg tcgcacctga ttgcccgaca     1440
ttatcgcgag cccatttata cccatataaa tcagcatcca tgttggaatt taatcgcggc     1500
ctcgagcaag acgtttcccg ttgaatatgg ctcataacac cccttgtatt actgtttatg     1560
taagcagaca gttttattgt tcatgatgat atatttttat cttgtgcaat gtaacatcag     1620
agattttgag acacaacgtg ctttccccc ccccccctgc aggtcgacgg atccggggaa     1680
ttcgtaatca tggtcatagc tgtttcctgt gtgaaattgt tatccgctca caattccaca     1740
caacatacga gccggaagca taaagtgtaa agcctggggt gcctaatgag tgagctaact     1800
cacattaatt gcgttgcgct cactgcccgc tttccagtcg ggaaacctgt cgtgccagct     1860
gcattaatga atcggccaac gcgcggggag aggcggtttg cgtattgggc gctcttccgc     1920
ttcctcgctc actgactcgc tgcgctcggt cgttcggctg cggcgagcgg tatcagctca     1980
ctcaaaggcg gtaatacggt tatccacaga atcaggggat aacgcaggaa agaacatgtg     2040
agcaaaaggc cagcaaaagg ccaggaaccg taaaaaggcc gcgttgctgg cgttttttcca     2100 taggctccgc cccctgacg agcatcacaa aaatcgacgc tcaagtcaga ggtggcgaaa     2160
cccgacagga ctataaagat accaggcgtt tcccctgga agctccctcg tgcgctctcc     2220
tgttccgacc ctgccgctta ccggatacct gtccgccttt ctcccttcgg gaagcgtggc     2280
gctttctcaa tgctcacgct gtaggtatct cagttcggtg taggtcgttc gctccaagct     2340
gggctgtgtg cacgaacccc cgttcagccc gaccgctgc gccttatccg gtaactatcg     2400
tcttgagtcc aacccggtaa gacacgactt atcgccactg gcagcagcca ctggtaacag     2460
gattagcaga gcgaggtatg taggcggtgc tacagagttc ttgaagtggt ggcctaacta     2520
cggctacact agaaggacag tatttggtat ctgcgctctg ctgaagccag ttaccttcgg     2580
aaaaagagtt ggtagctctt gatccggcaa acaaaccacc gctggtagcg gtggtttttt     2640
```

```
tgtttgcaag cagcagatta cgcgcagaaa aaaaggatct caagaagatc ctttgatctt    2700
ttctacgggg tctgacgctc agtggaacga aaactcacgt taagggattt tggtcatgag    2760
attatcaaaa aggatcttca cctagatcct tttaaattaa aaatgaagtt ttaaatcaat    2820
ctaaagtata tatgagtaaa cttggtctga cagttaccaa tgcttaatca gtgaggcacc    2880
tatctcagcg atctgtctat ttcgttcatc catagttgcc tgactccccg tcgtgtagat    2940
aactacgata cgggagggct taccatctgg ccccagtgct gcaatgatac cgcgagaccc    3000
acgctcaccg gctccagatt tatcagcaat aaaccagcca gccggaaggg ccgagcgcag    3060
aagtggtcct gcaactttat ccgcctccat ccagtctatt aattgttgcc gggaagctag    3120
agtaagtagt tcgccagtta atagtttgcg caacgttgtt gccattgcta caggcatcgt    3180
ggtgtcacgc tcgtcgtttg gtatggcttc attcagctcc ggttcccaac gatcaaggcg    3240
agttacatga tcccccatgt tgtgcaaaaa agcggttagc tccttcggtc ctccgatcgt    3300
tgtcagaagt aagttggccg cagtgttatc actcatggtt atggcagcac tgcataattc    3360
tcttactgtc atgccatccg taagatgctt ttctgtgact ggtgagtact caaccaagtc    3420
attctgagaa tagtgtatgc ggcgaccgag ttgctcttgc ccggcgtcaa tacgggataa    3480
taccgcgcca catagcagaa cttttaaaagt gctcatcatt ggaaaacgtt cttcggggcg    3540
aaaactctca aggatcttac cgctgttgag atccagttcg atgtaaccca ctcgtgcacc    3600
caactgatct tcagcatctt tactttcac cagcgtttct gggtgagcaa aacaggaag    3660 gcaaaatgcc gcaaaaaagg gaataagggc gacacggaaa tgttgaatac tcatactctt    3720 ccttttcaa tattattgaa gcatttatca gggttattgt ctcatgagcg gatacatatt    3780
tgaatgtatt tagaaaaata aacaaatagg ggttccgcgc acatttcccc gaaaagtgcc    3840
acctgacgtc taagaaacca ttattatcat gacattaacc tataaaaata ggcgtatcac    3900
gaggcccttt cgtc                                                      3914

<210> SEQ ID NO 38
<211> LENGTH: 57
<212> TYPE: DNA
<213> ORGANISM: artificial sequence
<220> FEATURE:
<223> OTHER INFORMATION: Primer sequence - chemically synthesized

<400> SEQUENCE: 38
gcgcgcgaat ctaaggagg aaaaaaaaat ggcaaataag ccaatgcaac cgatcac           57

<210> SEQ ID NO 39
<211> LENGTH: 44
<212> TYPE: DNA
<213> ORGANISM: artificial sequence
<220> FEATURE:
<223> OTHER INFORMATION: Primer Sequence - chemically synthesized

<400> SEQUENCE: 39
gcatgcaagc ttcattaagc agtagtatca gacgatacga tagc                        44

<210> SEQ ID NO 40
<211> LENGTH: 4962
<212> TYPE: DNA
<213> ORGANISM: artificial sequence
<220> FEATURE:
<223> OTHER INFORMATION: Expression Construct - chemically synthesized

<400> SEQUENCE: 40
ggctgtgcag gtcgtaaatc actgcataat tcgtgtcgct caaggcgcac tcccgttctg       60
```

```
gataatgttt tttgcgccga catcataacg gttctggcaa atattctgaa atgagctgtt    120
gacaattaat catcggctcg tataatgtgt ggaattgtga gcggataaca atttcacaca    180
ggaaacagaa ttcaggaggt aaaaaacgat ggcaaataag ccaatgcaac cgatcacatc    240
tacagcaaat aaaattgtgt ggtcggatcc aactcgttta tcaactacat tttcagcaag    300
tctgttacgc caacgtgtta aagttggtat agccgaactg aataatgttt caggtcaata    360
tgtatctgtt tataagcgtc ctgcacctaa accggaaggt tgtgcagatg cctgtgtcat    420
tatgccgaat gaaaaccaat ccattcgcac agtgatttca gggtcagccg aaaacttggc    480
taccttaaaa gcagaatggg aaactcacaa acgtaacgtt gacacactct tcgcgagcgg    540
caacgccggt ttgggtttcc ttgaccctac tgcggctatc gtatcgtctg atactactgc    600
ttaatgaagc ttggctgttt tggcggatga gagaagattt tcagcctgat acagattaaa    660
tcagaacgca gaagcggtct gataaaacag aatttgcctg gcggcagtag cgcggtggtc    720
ccacctgacc ccatgccgaa ctcagaagtg aaacgccgta gcgccgatgg tagtgtgggg    780
tctccccatg cgagagtagg gaactgccag gcatcaaata aaacgaaagg ctcagtcgaa    840
agactggggc tttcgtttta tctgttgttt gtcggtgaac gctctcctga gtaggacaaa    900
tccgccggga gcggatttga acgttgcgaa gcaacggccc ggagggtggc gggcaggacg    960
cccgccataa actgccaggc atcaaattaa gcagaaggcc atcctgacgg atggcctttt   1020 tgcgttcta caaactcttt tgtttatttt tctagagcca cgttgtgtct caaaatctct   1080
gatgttacat tgcacaagat aaaaatatat catcatgaac aataaaactg tctgcttaca   1140
taaacagtaa taaaggagt gttatgagcc atattcaacg ggaaacgtct tgctcgaggc   1200
cgcgattaaa ttccaacatg gatgctgatt tatatgggta taaatgggct cgcgataatg   1260
tcgggcaatc aggtgcgaca atctatcgat tgtatgggaa gcccgatgcg ccagagttgt   1320
ttctgaaaca tggcaaaggt agcgttgcca atgatgttac agatgagatg gtcagactaa   1380
actggctgac ggaatttatg cctcttccga ccatcaagca ttttatccgt actcctgatg   1440
atgcatggtt actcaccact gcgatccccg ggaaaacagc attccaggta ttagaagaat   1500
atcctgattc aggtgaaaat attgttgatg cgctggcagt gttcctgcgc cggttgcatt   1560
cgattcctgt ttgtaattgt ccttttaaca gcgatcgcgt atttcgtctc gctcaggcgc   1620
aatcacgaat gaataacggt ttggttgatg cgagtgattt tgatgacgag cgtaatggct   1680
ggcctgttga acaagtctgg aaagaaatgc ataagctttt gccattctca ccggattcag   1740
tcgtcactca tggtgatttc tcacttgata accttatttt tgacgagggg aaattaatag   1800
gttgtattga tgttggacga gtcggaatcg cagaccgata ccaggatctt gccatcctat   1860
ggaactgcct cggtgagttt tctccttcat tacagaaacg ctttttcaa aaatatggta   1920 ttgataatcc tgatatgaat aaattgcagt ttcatttgat gctcgatgag ttttctaaa   1980 cgcgtgacca agtttactca tatgtacttt agattgattt aaaacttcat ttttaattta   2040
aaaggatcta ggtgaagatc cttttgata atctcatgac caaaatccct taacgtgagt   2100
tttcgttcca ctgagcgtca gaccccgtag aaaagatcaa aggatcttct tgagatcctt   2160 ttttttctgcg cgtaatctgc tgcttgcaaa caaaaaaacc accgctacca gcggtggttt   2220
gtttgccgga tcaagagcta ccaactcttt ttccgaaggt aactggcttc agcagagcgc   2280
agataccaaa tactgtcctt ctagtgtagc cgtagttagg ccaccacttc aagaactctg   2340
tagcaccgcc tacatacctc gctctgctaa tcctgttacc agtggctgct gccagtggcg   2400
```

```
ataagtcgtg tcttaccggg ttggactcaa gacgatagtt accggataag gcgcagcggt    2460
cgggctgaac gggggttcg tgcacacagc ccagcttgga gcgaacgacc tacaccgaac     2520
tgagatacct acagcgtgag ctatgagaaa gcgccacgct ccccgaaggg agaaaggcgg    2580
acaggtatcc ggtaagcggc agggtcggaa caggagagcg cacgagggag ctcccagggg    2640
gaaacgcctg gtatctttat agtcctgtcg ggtttcgcca cctctgactt gagcgtcgat    2700
ttttgtgatg ctcgtcaggg gggcggagcc tatggaaaaa cgccagcaac gcggcctttt    2760
tacggttcct ggccttttgc tggccttttg ctcacatgtt ctttcctgcg ttatcccctg    2820
attctgtgga taaccgtatt accgcctttg agtgagctga taccgctcgc cgcagccgaa    2880
cgaccgagcg cagcgagtca gtgagcgagg aagcggaaga gcgcctgatg cggtattttc    2940
tccttacgca tctgtgcggt atttcacacc gcatatggtg cactctcagt acaatctgct    3000
ctgatgccgc atagttaagc cagtatacac tccgctatcg ctacgtgact gggtcatggc    3060
tgcgccccga cacccgccaa cacccgctga cgcgccctga cgggcttgtc tgctcccggc    3120
atccgcttac agacaagctg tgaccgtctc cgggagctgc atgtgtcaga ggttttcacc    3180
gtcatcaccg aaacgcgcga ggcagctgcg gtaaagctca tcagcgtggt cgtgaagcga    3240
ttcacagatg tctgcctgtt catccgcgtc cagctcgttg agtttctcca gaagcgttaa    3300
tgtctggctt ctgataaagc gggccatgtt aagggcggtt ttttcctgtt tggtcactga    3360
tgcctccgtg taagggggat ttctgttcat ggggtaatg ataccgatga acgagagag     3420
gatgctcacg atacgggtta ctgatgatga acatgcccgg ttactggaac gttgtgaggg    3480
taaacaactg gcgtatgga tgcggcggga ccagagaaaa atcactcagg gtcaatgcca    3540
gcgcttcgtt aatacagatg taggtgttcc acagggtagc cagcagcatc ctgcgatgca    3600
gatccggaac ataatggtgc agggcgctga cttccgcgtt tccagacttt acgaaacacg    3660
gaaaccgaag accattcatg ttgttgctca ggtcgcagac gttttgcagc agcagtcgct    3720
tcacgttcgc tcgcgtatcg gtgattcatt ctgctaacca gtaaggcaac cccgccagcc    3780
tagccgggtc ctcaacgaca ggagcacgat catgcgcacc cgtggccagg acccaacgct    3840
gcccgagatg cgccgcgtgc ggctgctgga gatggcggac gcgatggata tgttctgcca    3900
agggttggtt tgcgcattca cagttctccg caagaattga ttggctccaa ttcttggagt    3960
ggtgaatccg ttagcgaggt gccgccggct tccattcagg tcgaggtggc ccggctccat    4020
gcaccgcgac gcaacgcggg gaggcagaca aggtataggg cggcgcctac aatccatgcc    4080
aacccgttcc atgtgctcgc cgaggcggca taaatcgccg tgacgatcag cggtccaatg    4140
atcgaagtta ggctggtaag agccgcgagc gatccttgaa gctgtccctg atggtcgtca    4200
tctacctgcc tggacagcat ggcctgcaac gcgggcatcc cgatgccgcc ggaagcgaga    4260
agaatcataa tggggaaggc catccagcct cgcgtcgcga acgccagcaa gacgtagccc    4320
agcgcgtcgg ccgccatgcc ggcgataatg gcctgcttct cgccgaaacg tttggtggcg    4380
ggaccagtga cgaaggcttg agcgagggcg tgcaagattc cgaataccgc aagcgacagg    4440
ccgatcatcg tcgcgctcca gcgaaagcgg tcctcgccga aaatgaccca gagcgctgcc    4500
ggcacctgtc ctacgagttg catgataaag aagacagtca taagtgcggc gacgatagtc    4560
atgccccgcg cccaccggaa ggagctgact gggttgaagg ctctcaaggg catcggtcga    4620
cgctctccct tatgcgactc ctgcattagg aagcagccca gtagtaggtt gaggccgttg    4680
agcaccgccg ccgcaaggaa tggtgcatgc aaggagatgg cgcccaacag tccccggcc    4740
acggggcctg ccaccatacc cacgccgaaa caagcgctca tgagcccgaa gtggcgagcc    4800
```

-continued

```
cgatcttccc catcggtgat gtcggcgata taggcgccag caaccgcacc tgtggcgccg    4860
gtgatgccgg ccacgatgcg tccggcgtag aggatccggg cttatcgact gcacggtgca    4920
ccaatgcttc tggcgtcagg cagccatcgg aagctgtggt at                       4962
```